(12) United States Patent
De Vuyst et al.

(10) Patent No.: US 7,615,367 B2
(45) Date of Patent: Nov. 10, 2009

(54) STREPTOCOCCUS THERMOPHILUS STRAINS PRODUCING STABLE HIGH-MOLECULAR-MASS EXOPOLYSACCHARIDES

(75) Inventors: Luc De Vuyst, Erembodegem (BE); Frederik Vaningelgem, Meise (BE)

(73) Assignee: Vrije Universiteit Brussel, Brussels (BE)

( * ) Notice: Subject to any disclaimer, the term of this patent is extended or adjusted under 35 U.S.C. 154(b) by 289 days.

(21) Appl. No.: 10/516,580

(22) PCT Filed: Jun. 3, 2003

(86) PCT No.: PCT/EP03/05805

§ 371 (c)(1),
(2), (4) Date: Jan. 24, 2005

(87) PCT Pub. No.: WO03/102204

PCT Pub. Date: Dec. 11, 2003

(65) Prior Publication Data

US 2005/0208630 A1    Sep. 22, 2005

(30) Foreign Application Priority Data

Jun. 3, 2002    (EP) .................. 02447104

(51) Int. Cl.
C12N 1/20 (2006.01)
(52) U.S. Cl. .................................. 435/253.4
(58) Field of Classification Search .............. 435/253.4
See application file for complete search history.

(56) References Cited

U.S. PATENT DOCUMENTS 5,965,127 A * 10/1999 Lemoine et al. .......... 424/93.44
6,033,691 A *  3/2000 Cravero ....................... 426/43

FOREIGN PATENT DOCUMENTS

EP    0 889 135 A1    1/1999
EP    0 889 136 A1    1/1999

OTHER PUBLICATIONS

Faber, et al. "The Exopolysaccharides Produced by *Streptococcus thermophilus* Rs and Sts Have the Same Repeating Unit but Differ in Viscosity of Their Milk Cultures," *Carbohydrate Research*, vol. 310, pp. 269-276, 1998.

Ariga, et al. "Extracellular Polysaccharide from Encapsulated *Streptococcus salivarius* subsp. *thermophilus* OR 901 Isolated from Commercial Yogurt," *Journal of Food Science*, vol. 57, No. 3, pp. 625-628, 1992.

Briczinski, et al. "Production of an Exopolysaccharide-Containing Whey Protein Concentrate by Fermentation of Whey," *Journal of Dairy Science*, vol. 85, pp. 3189-3197, 2002.

Degeest, et al. "Indication that the Nitrogen Source Influences Both Amount and Size of Exopolysaccharides Produced by *Streptococcus thermophilus* LY03 and Modelling of the Bacterial Growth and Exopolysaccharide Production in an Complex Medium," *Applied and Environmental Microbiology*, vol. 65, No. 7, pp. 2863-2870, Jul. 1999.

Hassan, et al. "Factors Affecting Capsule Size and Production by Lactic Acid Bacteria Used as Dairy Starter Cultures," *International Journal of Food Microbiology*, vol. 64, pp. 199-203, 2001.

Degeest, et al. "Optimization of the Production and Isolation of Exopolysaccharides from *Streptococcus thermophilus* and Strong Evidence for Growth-Associated Biosynthesis," *Mededelingen Faculteit Landbouwkundige en Toegepaste Biologische*, vol. 62, No. 4A-B, pp. 1199-1206, 1997.

Cerning, et al. "Isolation and Characterization of Exopolysaccharides from Slime-Forming Mesophilic Lactic Acid Bacteria," *Journal of Dairy Science*, vol. 75, pp. 692-699, 1992.

Gancel, et al. "Exopolysaccharide Production by *Streptococcus salivarius* ssp. *thermophilus* Cultures. 1. Conditions of Production," *Journal of Dairy Science*, vol. 77, pp. 685-688, 1994.

International Search Report completed on Jan. 14, 2004 and issued to a related foreign application.

Budd, et al. "Structural Characterisation of the Exocellular Polysaccharide Produced by *Streptococcus thermophilus* OR 901," *Carbohydrate Research*, vol. 301, pp. 41-50, 1997.

* cited by examiner

*Primary Examiner*—L Blaine Lankford
*Assistant Examiner*—Susan E. Fernandez
(74) *Attorney, Agent, or Firm*—Knobbe, Martens, Olson & Bear, LLP

(57) ABSTRACT

The invention relates to the field of exopolysaccharide producing lactic acid bacteria. The invention relates to methods and culture media for producing large amounts of exopolysaccharides in safe and simple fermentation conditions. The invention more specifically relates to the characterization of a *Streptococcus thermophilus* ST 111 strain producing a stable high-molecular-mass heteropolysaccharide, its use in functional starter cultures and its use in food fermentation processes such as processes producing milk products, yoghurt and cheese for texture improvement and decreasing syneresis during fermentation and in the fermented product.

14 Claims, 7 Drawing Sheets

Figure 1:
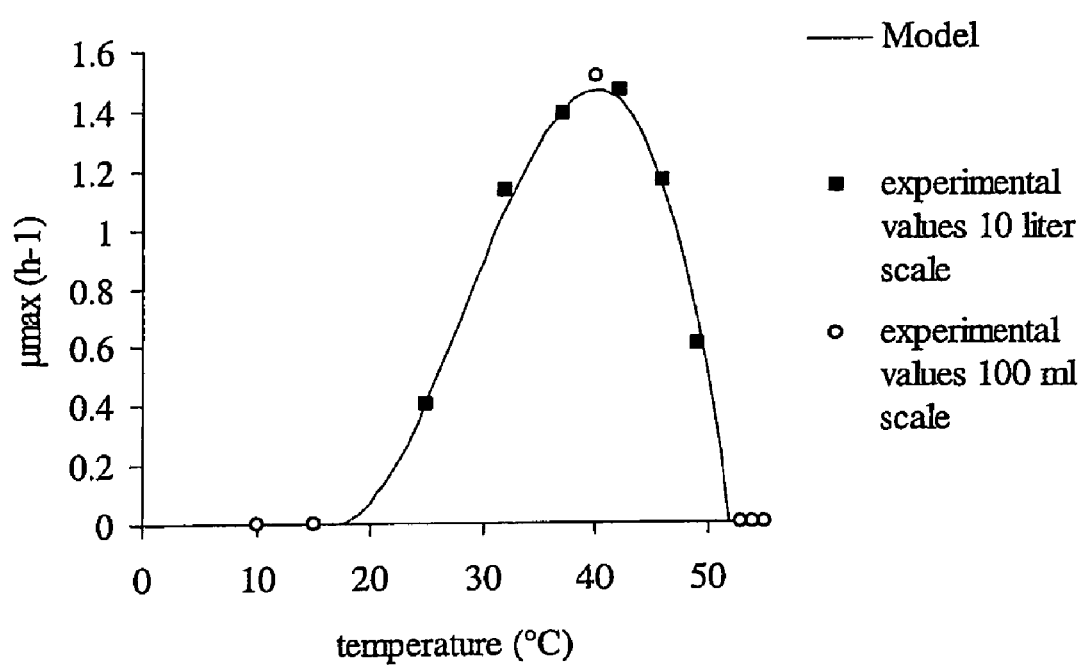

STREPTOCOCCUS THERMOPHILUS STRAINS PRODUCING STABLE HIGH-MOLECULAR-MASS EXOPOLYSACCHARIDES

RELATED APPLICATIONS

This application is the U.S. National Phase under 35 U.S.C. § 371 International Application PCT/EP03/05805, filed Jun. 3, 2003, which claims priority of EP 02447104.7, filed Jun. 3, 2002.

FIELD OF THE INVENTION

The invention relates to the field of methods for producing large amounts of exopolysaccharides. The invention more specific relates to the characterization of a *Streptococcus thermophilus* strain producing a stable high-molecular-mass heteropolysaccharide, and to the use of said *Streptococcus thermophilus* strain in and as functional starter culture and in the production of dairy products.

BACKGROUND OF THE INVENTION

Sugar polymers or exopolysaccharides (EPS) produced by lactic acid bacteria (LAB) can be subdivided into two groups: homopolysaccharides and heteropolysaccharides (Cerning, 1990, 1995; De Vuyst & Degeest, 1999). Four groups of homopolysaccharides can be distinguished: α-D-glucans, β-D-glucans, β-D-fructans, and others like polygalactan (Monsan et al., 2001). Strain-specific differences occur that depend on the degree of branching and the different linking sides. Heteropolysaccharides are produced by LAB in a greater variety concerning chemical composition, monomer ratio, molecular mass and molecular structure (De Vuyst et al., 2001; Faber et al., 2002). Their repeating units most often contain a combination of D-glucose, D-galactose, and L-rhamnose, and, in a few cases, fucose, nononic acid, ribose, acetylated amino sugars and glucuronic acid, as well as non-carbohydrate substituents such as phosphate, acetyl and glycerol. Heteropolysaccharides receive renewed interest because of their functional role in food systems such as enhancement of viscosity, suspension of particulates, inhibition of syneresis, stabilization, and emulsification. For instance, the use of ropy, EPS-producing LAB strains is applied in the manufacture of yoghurt to obtain a smooth texture and a good mouthfeel.

The in situ production of these sugar polymers by the yoghurt bacteria is applied as an alternative to the addition of animal hydrocolloids (gelatine and casein) or chemically modified plant carbohydrates (starch, pectin, guar gum, etc.). EPS from non-GRAS (Generally Recognized As Safe) microbial origin (xanthan or gellan) are used in foods as well. However, not all these food additives are allowed in all countries.

Furthermore, the amounts of EPS produced by LAB are low and their production is unstable, particularly in milk (Degeest et al., 2001b).

Due to the low amount of EPS produced by LAB strains and the transitory nature of the exopolysaccharide trait (Cerning, 1990), the use of these compounds as food-grade additives is still limited. Until present, only dextran homopolysaccharides from LAB found industrial applications, albeit in the non-food sector (Monsan et al., 2001).

Further, the construction of genetically modified strains might allow the production of higher levels of EPS or new biopolymers. However, the use of genetically modified microorganisms in the food industry is hindered by the hostility of the consumer. Therefore there is a growing need for the optimalisation of fermentations with respect to physical and environmental factors, with rationally selected strains for use in the food industry.

There is further an industrial need for strains that produce high amounts of stable EPS in a safe and simple environment.

SUMMARY OF THE INVENTION

The present invention relates to a *Streptococcus thermophilus* ST 111 strain as deposited on May 29, 2002 under the accession number LMG P-21524 at the Belgian Coordinated Collections of Microorganisms (BCCM), and strains substantially similar thereto, encoding exopolysaccharide production.

The present invention relates to a *Streptococcus thermophilus* ST 111 strain as deposited on May 29, 2002 under the accession number LMG P-21524, encoding exopolysaccharide production.

The present invention further relates to a functional starter culture or a co-culture comprising an exopolysaccharide-producing lactic acid bacterial strain as described above.

According to another embodiment the invention relates to the use of a functional starter culture or a co-culture as described above for the production of high-molecular-mass heteropolysaccharides of at least $2.10^6$ Dalton during fermentation, preferably for the fermentation of a food product.

The invention also relates to a method for preparing an exopolysaccharide comprising culturing an exopolysaccharide-producing lactic acid bacterial strain in a medium comprising milk and lactalbumin hydrolysate, or in a medium comprising milk and lactalbumin hydrolysate and at least one additional mono- or disaccharide.

According to another embodiment, the methods of the invention are characterized in that at least 60% or 80% by weight of said exopolysaccharide has a molecular mass of at least $2.10^6$ Dalton. Preferably, said said exopolysaccharide has the following structure:

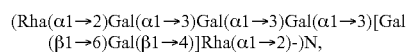
$$(Rha(\alpha 1 \rightarrow 2)Gal(\alpha 1 \rightarrow 3)Gal(\alpha 1 \rightarrow 3)Gal(\alpha 1 \rightarrow 3)[Gal(\beta 1 \rightarrow 6)Gal(\beta 1 \rightarrow 4)]Rha(\alpha 1 \rightarrow 2)\text{-})N,$$

wherein N is between 800 and 7000.

According to a further embodiment, said monosaccharide is chosen from glucose, galactose or fructose, or said disaccharide is sucrose.

In a more specific embodiment, the invention relates to any method described above wherein a strain according to claim 1 is used.

The invention also relates to a high-molecular-mass exopolysaccharide of at least $2.10^6$ Dalton obtainable by any of the methods of the invention.

According to another embodiment the invention relates to a method for improving the texture of a fermented product comprising adding at the start of or during the fermentation process, a culture of the *Streptococcus thermophilus* ST 111 strain of claim 1.

According to another embodiment the invention relates to a method for improvement of water retention in a fermented product comprising adding at the start of or during the fermentation process, a culture of *Streptococcus thermophilus* ST 111 strain of claim 1.

According to another embodiment the invention relates to a method for decreasing syneresis of a fermented product comprising adding at the start of or during the fermentation process, a culture of the *Streptococcus thermophilus* ST 111 strain of claim 1.

According to another embodiment the invention relates to a method for improvement of water retention during the fermentation process comprising adding at the start of or during the fermentation process, a culture of the *Streptococcus thermophilus* ST 111 strain of claim 1.

According to another embodiment the invention relates to a method for producing a dairy product comprising adding to the initial dairy product starter culture or adding during the fermentation process, a culture of the *Streptococcus thermophilus* ST 111 strain according to claim 1.

The invention also relates to the use of a *Streptococcus thermophilus* ST 111 strain of claim 1 for the production of high-molecular-mass heteropolysaccharides of at least $10^6$ Dalton in food fermentation processes.

The invention also relates to the use of a functional starter culture or a co-culture comprising a *Streptococcus thermophilus* ST 111 strain of claim 1 wherein said food product is a dairy product, preferably said dairy product is chosen from the group of milk products, fermented milk drinks, yoghurts, cheeses, sour cream, whipped toppings, quark and kefir.

The invention further relates to any dairy product obtainable by any of the methods of the invention, preferably said dairy product is a Mozzarella cheese.

According to a still further embodiment the invention relates to a functional starter culture for the fermentation of a yoghurt comprising a culture of the *Streptococcus* thermophilus ST 111 strain of claim 1 and a culture of *Lactobacillus delbrueckii* subsp. *bulgaricus*.

The invention also relates to the use of a high-molecular-mass exopolysaccharide of at least $2.10^6$ obtainable by any of the methods of the invention as an additive to a fermented or non-fermented food product.

The invention also relates to the use of a high-molecular-mass exopolysaccharide of at igh-molecular-mass exopolysaccharide of at least $2.10^6$ obtainable by any of the methods of the invention as an additive to a fermented or non-fermented food product for improving water retention of the food product, and/or for decreasing syneresis, and/or for improving the texture of said food product.

The invention further relates to any of the uses described above wherein said food product is chosen from the group of milk products, fermented milk drinks, yoghurts, cheeses, soups, sour cream, whipped toppings, quark, kefir and sauces.

According to another embodiment the invention relates to a functional starter culture or a co-culture comprising an exopolysaccharide-producing lactic acid bacterial strain for the production of high-molecular-mass heteropolysaccharides of at least $2.10^6$ Dalton during fermentation.

DETAILED DESCRIPTION OF THE INVENTION

The present inventors identified a novel exopolysaccharide (EPS) producing *Streptococcus thermophilus* strain, named ST 111, which they isolated from an artisanally produced Romanian yoghurt.

Therefore, according to a first embodiment, the invention relates to a *Streptococcus thermophilus* ST 111 strain as deposited on May 29, 2002 under the accession number LMG P-21524 and strains substantially similar thereto encoding exopolysaccharide production.

The inventors elucidated the structure of this pure, high-molecular-mass exopolysaccharides produced by *Streptococcus thermophilus* ST 111 by nuclear magnetic resonance (NMR) spectroscopy. The production of EPS by *S. thermophilus* ST 111 shows a high selectivity with regard to said heteropolysaccharide which is essentially composed of repeating heptasaccharide units comprising galactose and rhamnose in a 5:2 ratio.

The term "exopolysaccharide" refers to homopolysaccharides as well as to heteropolysaccharides. "Heteropolysaccharides" are intracellularly synthesized and extracellularly secreted sugar polymers composed of a repeating unit that contains two or more different monosaccharides. "Homopolysaccharides" are composed of one type of monosaccharide.

The variation in monomers that build up the repeating units of EPS produced by LAB is rather restricted (De Vuyst & Degeest, 1999; De Vuyst et al., 2001). D-galactose, D-glucose and L-rhamnose are almost always present, but in different ratios. *S. thermophilus* ST 111 produces a heteropolysaccharide composed of repeating heptasaccharide units comprising galactose and rhamnose in a 5:2 ratio. The NMR structure of the heptasaccharide repeating unit is represented in FIG. 3.

The inventors further identified the EPS produced by *S. thermophilus* ST 111 as a stable heteropolymer EPS with a molecular mass above $2.10^6$ Dalton. The production of EPS by *S. thermophilus* ST 111 shows a high selectivity with regard to said heteropolysaccharide composed of repeating heptasaccharide units comprising galactose and rhamnose in a 5:2 ratio.

Figure 5:
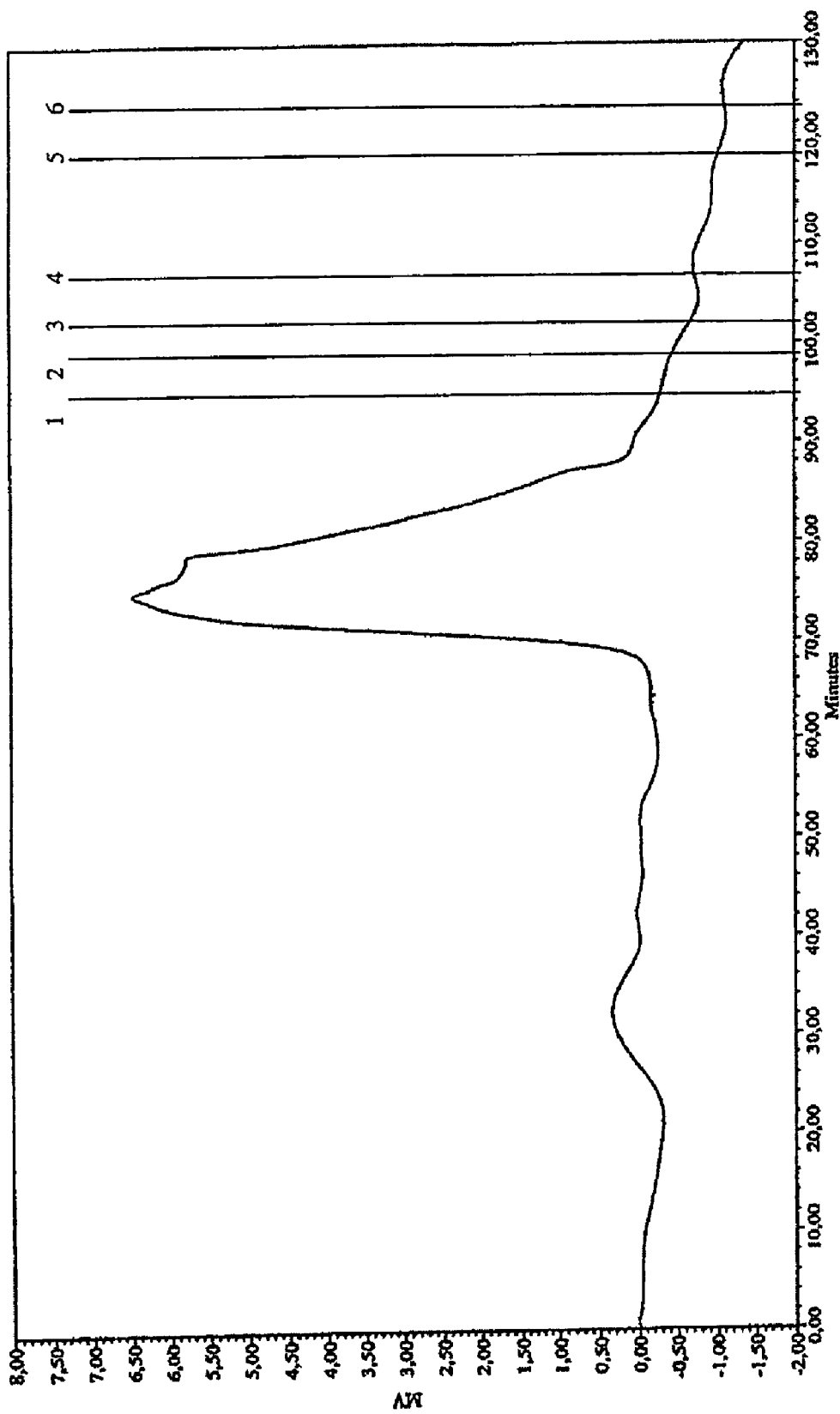

The invention thus also relates to a *Streptococcus thermophilus* ST 111 strain and strains substantially similar thereto capable of producing a high-molecular-mass exopolysaccharide, such as essentially the one represented in FIG. 3 and FIG. 5. According to a further embodiment the invention relates to a method for preparing an exopolysaccharide comprising the steps of (i) providing an exopolysaccharide-producing lactic acid bacterial strain, (ii) culturing said strain under conditions allowing production of exopolysaccharide, and optionally (iii) isolating the exopolysaccharide from the culture medium.

In one embodiment of the invention such method can be used for the production of an EPS or an EPS-containing product, either of which can be used as an additive for food products. In another embodiment the method can be used for in situ production of an EPS comprising growing a *Streptococcus thermophilus* ST 111 strain or a strain substantially similar thereto in a dairy liquid medium under conditions whereby said EPS is formed until the culture has reached a relative high density of said streptococci, for instance in the order of $10^7$ to $10^{12}$ colony forming units (CFU) per ml, preferably from $10^9$ to $10^{10}$ CFU per ml.

Figure 3A:
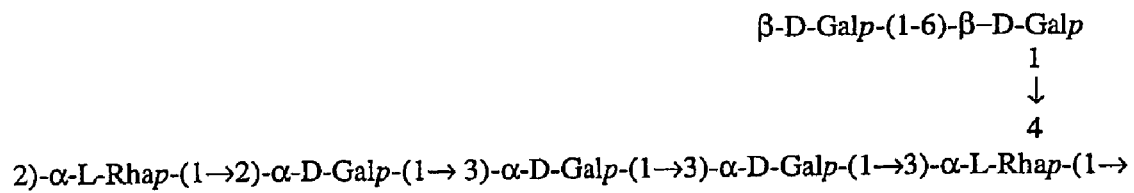

According to a further embodiment the invention thus relates to a process for in situ production of an exopolysaccharide, essentially a heteropolysaccharide having a subunit structure as represented in FIG. 3A, comprising growing *S. thermophilus* ST 111 in an edible medium such as a dairy liquid under conditional whereby EPS is formed until the number of Streptococci is in the order of $10^7$ to $10^{12}$ CFU per ml, preferably from $10^9$ to $10^{10}$ CFU per ml.

The density of a culture is measured by its optical density (OD). However an indicative measure for representing the growth and/or fitness of a culture during fermentation is the maximum specific growth rate $\mu_{max}$ ($h^{-1}$) which is calculated as the maximum slope from the linearised values of the optical density as a function of the fermentation time (h). For the aims of the present invention it is desirable that the fermentation culture has a high $\mu_{max}$, preferably higher than 0.4 ($h^{-1}$), more preferably at least 0.8 ($h^{-1}$), 1.0 ($h^{-1}$), 1.1 ($h^{-1}$), 1.2 ($h^{-1}$), 1.3 ($h^{-1}$), 1.4 ($h^{-1}$), 1.5 ($h^{-1}$), 1.6 ($h^{-1}$), 1.7 ($h^{-1}$), 1.8 ($h^{-1}$), 1.9 ($h^{-1}$), or at least 2($h^{-1}$) or more.

According to a further embodiment the invention thus relates to a process for in situ production of an exopolysaccharide, essentially a heteropolysaccharide having a subunit structure as represented In FIG. 3A, comprising growing *S. thermophilus* ST 111 in an edible medium such as a dairy liquid under conditions whereby EPS is formed until the maximum specific growth rate $\mu_{max}$ of the culture reaches at least 0.4 ($h^{-1}$), more preferably at least 0.8 ($h^{-1}$), 1.0 ($h^{-1}$), at least 1.5 ($h^{-1}$), at least 1.8 ($h^{-1}$), at least 1.9 ($h^{-1}$), or at least 2 ($h^{-1}$) or more.

An EPS producing *Streptococcus thermophilus* strain can impart a ropy character and/or a smooth and creamy texture to the fermented product. Furthermore, the EPS provides to the resulting fermented food product or to the food product comprising EPS as an additive other highly desired properties such as enhancing the viscosity, which leads to an improved texture build-up and to less solid products (e.g. rheological properties); or such as improving the water binding capacity which leads to no or less syneresis.

EPS can also display biological activities which are especially advantageous for human or animal health such as its antitumour, probiotic, cholesterol lowering, anti-ulcer activity.

The "texture" of a product, as meant herein, is due to the existence of a protein gel, mainly constituted of caseins, the interactions between proteins and polysaccharides, the presence of bacterial cells, the binding of hydratation water that reduces the amount of free water molecules and consequently increases the apparent concentration of the EPS in the serum phase. Bacterial EPS influence the rheology and texture of fermented products. Therefore, EPS may act as texturizers and stabilizers avoiding the use of food additives. An increased viscosity of the food product not only results in a pleasant mouthfeel but also contributes to an increased taste perception (longer residence time in the mouth). The aim of using EPS producing strains in the production of fermented food products or the use of EPS as an additive is to obtain an appealing visual appearance (gloss) of a product, to prevent syneresis, to have a creamy and firm texture, and to give a pleasant mouthfeel. However, since production of one kind of EPS may not satisfy all texture specifications, the production of several startercultures may be required.

The term "syneresis" means separation of the serum (whey) in fermented milk products and is usually visible on top of fermented milk products. Syneresis preferably should not occur and can be avoided by the methods of the present invention.

Therefore, the invention relates to a method for improving the texture of a fermented product comprising adding during the fermentation process or adding to the fermentation starter culture, a culture of an exopolysaccharide-producing lactic acid bacterial strain producing a high-molecular-mass heteropolysaccharide of at least $2.10^6$ Dalton.

It should be understood that the exopolysaccharide-producing lactic acid bacterial strain may be added at different moments during the fermentation process. According to one embodiment of the invention the EPS-producing LAB is the sole bacterium used in the fermentation process and is used as a starter culture for the fermentation. According to another embodiment, the EPS-producing LAB is present as a co-culture in the initial starter culture. According to still another embodiment, the EPS-producing LAB can be added at any time during the fermentation process. In the latter embodiment, optionally other LAB strains can be added providing additional functionalities, such as improvement of taste or odor or aroma.

The term "culture" refers to any sample or specimen which is suspected of containing one or more microorganisms. Further, the term culture as used herein also relates to "starter culture", "functional starter culture" and "co-culture".

The invention further relates to a method for improvement of water retention during the fermentation process comprising adding during the fermentation process or adding to the fermentation starter culture, a culture of an exopolysaccharide-producing lactic acid bacterial strain producing a high-molecular-mass heteropolysaccharide of at least $2.10^6$ Dalton.

According to another embodiment the invention relates to a method for improvement of water retention in a fermented product comprising adding during the fermentation process or to the fermentation starter culture, a culture of an exopolysaccharide-producing lactic acid bacterial strain producing a high-molecular-mass heteropolysaccharide of at least $2.10^6$ Dalton.

The invention further relates to a method for decreasing syneresis of a fermented product comprising adding during the fermentation process or to the fermentation starter culture, a culture of an exopolysaccharide-producing lactic acid bacterial strain producing a high-molecular-mass heteropolysaccharide of at least $2.10^6$ Dalton.

Further, the invention relates to any of the above mentioned methods wherein a culture of the *Streptococcus thermophilus* strain ST 111 of the invention is added to the fermentation.

One of the interesting embodiments of the invention relates to a method for producing a dairy product comprising adding to the initial dairy product starter culture or adding during the fermentation process, a culture of the *Streptococcus thermophilus* ST 111 strain of the invention.

The inventors further studied the influence of temperature, pH, and medium composition on the production, molecular mass and monomer composition of the EPS. They found that maximum EPS production with *S. thermophilus* ST 111 is at temperatures optimal for growth.

As such, the "conditions" in the method above comprise culturing EPS producing LAB, for instance *S. thermophilus* ST 111, at temperatures between 20° C. and 49° C. or between 20° C. and 46° C. or between 25° C. and 46° C., preferably at temperatures between 32° C. and 42° C. As shown in the Examples section, the most interesting temperatures for culturing LAB in order to produce high amounts of EPS is 37° C. or 42° C.

Further, both growth and EPS production were influenced by the pH value of the medium. As such, the "conditions" in the method above comprise culturing EPS producing LAB, for instance *S. thermophilus* ST 111, at a pH between 5.0 and 6.2 or between 5.3 and 7.5, preferably at a pH between 5.5 and 6.7. As shown in the Examples section, the most interesting pHs for culturing LAB in order to produce high amounts of EPS are 5.8, 6.2 or 6.6.

In fermentation at a controlled temperature of 42° C. and at a constant pH of 6.2, *S. thermophilus* ST 111 shows satisfying growth and EPS production.

Under the conditions described above, a high production of exopolysaccharide was obtained. In most conditions, a production of at least 3 $gl^{-1}$ was obtained.

The inventors further found that the monomer composition of said high-molecular-mass exopolysaccharide produced by *S. thermophilus* ST 111 was not influenced by the physical growth conditions, such as pH and temperature. FIG. 5 represents a gel permeation chromatogram of EPS produced by *S. thermophilus* ST 111 by the methods described herein, showing a distinct peak of the pure EPS with negligible or no degradation into lower molecular mass products.

The invention thus relates to the above method characterized in that a stable high-molecular-mass exopolysaccharide production is obtained, with no or negligible degradation into lower molecular mass products. Preferably the above methods are characterized in that at least 60%, 65% or 80%, or more preferably at least 85% or 90% or 95% of said exopolysaccharide has a molecular mass of at least $10^6$ Dalton or at least $2.10^6$ Dalton, more preferably at least 2.5 times $10^6$ Dalton, $3.10^6$ Dalton, 3.5 times $10^6$ Dalton, most preferably at least $4.10^6$ Dalton, $5.10^6$ Dalton, $6.10^6$, $7.10^6$, $8.10^6$ Dalton or more.

The invention also relates to a method characterized in that said exopolysaccharide is a polymer of heptasaccharide units composed of galactose and rhamnose in a 5:2 ratio, for instance having the structure as depicted in FIG. 3:

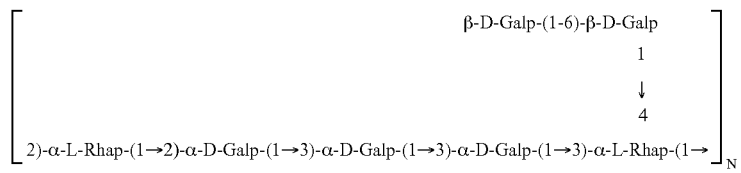

wherein N is between 800 and 5000, preferably between 814 and 4886, or wherein N is at least 1000, 1500, 2000, 2500, 3000, 3500, 4000, 4500, 5000, 5500, 6000, 6500 or at least 7000 or any number in-between these numbers.

Another way of representing the structure of the high-molecular-mass exopolysaccharide of the invention is as follows: (Rha(α1→2)Gal(α1→3)Gal(α1→3)Gal(α1→3)[Gal(β1→6) Gal(β1→4)]Rha(α1→2)-)N or (Rhaα2Galα3Galα3Galα3(Galβ6Galβ4)Rhaα2-)N, with N having the same meaning as defined above.

Although *Streptococcus thermophilus* ST 111 grows only slowly in milk when it is not enriched with additional energy or nitrogen sources such as tryptone or casamino acids, higher yields of EPS are achieved when growing *Streptococcus thermophilus* ST 111 in commercial available MRS, M17 or HJL medium. However, these media are not attractive for industrial use because they all contain contaminating (undesired) polysaccharide material from medium constituents which remain in the produced and isolated EPS fraction. Furthermore the above-mentioned commercial available media are not the ones commonly used in industrial fermentation processes.

Therefore, a suitable medium for the preparation of high-molecular-mass exopolysaccharide is milk medium enriched with lactalbumine hydrolysate. It is herein demonstrated that a significant elevated production of EPS can be obtained in milk medium containing only 1.6% of lactalbumine hydrolysate as an additional ingredient. Surprisingly, an even more elevated production was obtained when the medium was supplemented with at least one additional sugar (or carbon) source, such as a mono- or disaccharide. In the Examples sections it is shown that an exceptional amount of more than 3 g of polymer dry mass (PDM) of EPS per liter medium could be recovered when sucrose was used as an additional carbohydrate source in milk enriched with lactalbumine hydrolysate.

Both structure and molecular mass influences the rheological properties of a polysaccharide. The high-molecular-mass EPS produced by the LAB of the present invention has excellent rheological properties, as illustrated in Example 9, for instance for the high-molecular-mass EPS produced by *Streptococcus thermophilus* ST 111.

*Streptococcus thermophilus* ST 111 strain produced a stable high-molecular-mass heteropolysaccharide in milk of which the production can be increased significantly by addition of ingredients such as lactalbumine hydrolysate. An even higher production was found when, in addition to lactalbumine hydrolysate, a mono- or disaccharide was added to the milk medium, such as for instance glucose, galactose, fructose, or sucrose.

The term "milk" as used herein can be ordinary milk standardized to a particular protein and/or fat content according to the desired end product and the process to be applied. The milk can also be reconstituted milk from powdered milk, for instance commercially available skimmed milk powder at commonly used concentrations. The milk can include other materials e.g. buttermilk, skim milk, butterfat, vegetable fat etc. The milk may have been pasteurized and/or treated at high temperature and/or homogenized. The milk may be obtained from any mammal known to produce sufficient amounts of milk for use in food industry. Mammals which produce milk for industrial or artisanal use are for instance cows, sheep, goats, horses, buffalo's, etc. It should be understood that this list is non-exhaustive. Milk as used in the processes of the invention may also be derived from plants, for instance from Soya.

"Lactalbumine hydrolysate" is an enzymatically hydrolysed protein derived from whey.

The invention thus relates to any of the methods described herein comprising culturing exopolysaccharide-producing lactic acid bacterial strain in a medium comprising milk and lactalbumine hydrolysate. Said lactalbumine hydrolysate may be present in the medium at a concentration between 0% and 16%, preferably at a concentration of 0%, 0.5%, 1%, 1.5%, 1.6%, 2%, 3%, 4%, 5%, 6%, 7%, 8%, 9%, 10%, 11%, 12%, 13%, 14%, 15%, 16% or any concentration in-between these units.

According to a more interesting embodiment, the exopolysaccharide-producing lactic acid bacteria are grown in a medium comprising milk, lactalbumine hydrolysate and at least one additional mono- or disaccharide carbon (or energy) source, for instance fructose and/or galactose, more preferably glucose and/or sucrose.

It should be understood that any other mono- or disaccharide can be used as an additive to the milk in the methods of the invention, as long as it may be demonstrated that this results in an additional elevation of the EPS production when compared to the EPS produced in milk with lactalbumine hydrolysate alone. Furthermore the concentration of said additional carbon (or energy) source used in the milk medium above may be between 0% and 10%, preferably at a concentration of 0%, 0.5%, 1%, 1.5%, 1.6%, 2%, 3%, 4%, 5%, 6%, 7%, 8%, 9%, 10%, or any concentration in-between these units.

This modified milk medium thus has the advantage to enhance the bacterial growth and EPS production without the interference of medium components with the isolation of EPS. The invention further relates to any of the above described methods of the invention wherein a culture of the Streptococcus thermophilus ST 111 strain is used.

According to a preferred embodiment the invention relates to a method for preparing an exopolysaccharide comprising culturing Streptococcus thermophilus ST 111 strain as deposited on May 29, 2002 under the accession number LMG P-21524, in a medium comprising milk and lactalbumine hydrolysate, optionally supplemented with at least one additional mono- or disaccharide.

The invention further relates to the use of Streptococcus thermophilus ST 111 in food fermentations such as processes producing fermented milk products, yoghurt and cheese for texture improvement and for decreasing syneresis during fermentation and in the fermented product.

According to a further embodiment, the EPS can optionally be isolated after fermentation by any suitable technique, e.g. as described in the Examples Section. Due to the high production under the conditions herein defined, a large part of the produced EPS appears as a "floating" fraction after aceton precipitation as described in the Examples section. Therefore, a very simple and easy-to-perform isolation technique can be applied essentially consisting of removal of the floating EPS material by spinning the EPS on a rod or by skimming off the floating fraction from the solution after aceton precipitation.

The invention further relates to a high-molecular-mass exopolysaccharide of at least $2.10^6$ Dalton obtainable by any of the methods described herein.

The invention also relates to a high-molecular-mass exopolysaccharide of at least $2.10^6$ Dalton obtained by any of the methods herein described.

The surprisingly enhanced production of high-molecular-mass heteropolysaccharides when Streptococcus thermophilus ST 111 is grown in a natural food system, such as milk supplemented with lactalbumine hydrolysate and at least one additional carbon (or energy) source, for instance at least one mono- or disaccharide as demonstrated by the present inventors, makes the potential use of this strain in fermentation processes more challenging, because these mono or disaccharides are readily used as sweeteners in fermented milk products.

According to a specific embodiment the invention thus relates to the use of a lactic acid bacterial strain for the production of high-molecular-mass heteropolysaccharides of at least $2.10^6$ Dalton in food fermentation processes, for instance the Streptococcus thermophilus ST 111 strain as defined in the invention.

The production of fermented food is based on the use of starter cultures. The term "starter culture" refers to microorganisms that initiate a rapid acidification of the raw material, contributing to prolonged shelf life, an improved texture, and a desirable aromatic and sensorial profile of the end product. Through rational selection of bacterial strains it is possible to suppress undesirable and express desirable properties of starter cultures. Recently, the use of functional starter cultures for the food fermentation industry is being explored. Examples are the insertion of rationally selected strains, such as the strains of the invention, as starter culture or co-culture in fermentation processes to help to achieve an in situ expression of the desired property, while maintaining a perfectly natural product.

"Functional starter cultures" as used herein thus refers to starter cultures that possess at least one inherent, functional property. In the present invention starter cultures that produce large amounts of exopolysaccharides, for instance high-molecular-mass heteropolysaccharides of more than $2.10^6$ Dalton, for instance having a monomer composition as illustrated in FIG. 3, such as produced by Streptococcus thermophilus strain ST 111, are examples of functional starter cultures. The secreted heteropolysaccharides may impart to the fermented end product for instance a more viscous or thicker or smooth texture, or for instance a good mouthfeel.

It should be clear that the present invention can be reduced to practice at least in each of the fermentation processes illustrated in Table 7. The invention thus relates to the use of an exopolysaccharide-producing lactic acid bacterium, for instance Streptococcus thermophilus ST 111 for the production of large amounts of high-molecular-mass heteropolysaccharides in at least one of the food fermentation processes with their associated microorganisms as shown in Table 7.

The present invention thus also relates to a starter culture as described above for the fermentation of a food product. Said food product can be any fermented food product as mentioned in Table 7. In an interesting embodiment said food product is chosen from a milk product, a fermented milk product, yoghurt, or a cheese.

It should be clear that whenever herein the expression "fermented product" or "fermented food product" is used, each of the fermented food products mentioned in Table 7 could be meant, depending on the type of fermentation used. Furthermore it should be clear that this list of fermented food products is a non-exhaustive list.

In case the exopolysaccharide-producing lactic acid bacterial strains, such as Streptococcus thermophilus ST 111, are added to aid to the fermentation/acidification of specific food products, the term "starter culture" is used herein. However, in case said exopolysaccharide-producing lactic acid bacterial strains only play a minor role in the fermentation process, and their presence is mainly determined by their capacity to confer an additional functional property to the starter culture, the term "co-culture" or "adjuvant culture" is mainly used.

Therefore, the present invention also relates to a functional starter culture comprising an exopolysaccharide-producing lactic acid bacterial strain for the production of high-molecular-mass heteropolysaccharides of at least $2.10^6$ Dalton during fermentation.

As already described earlier, the production of fermented food is based on the use of starter cultures. Interesting starter cultures are functional starter cultures that possess at least one inherent functional property. According to the present invention, a functional starter culture is a starter culture comprising a Streptococcus thermophilus ST 111 strain as defined herein for the production of high-molecular-mass heteropolysaccharides.

The invention further also relates to a co-culture comprising an exopolysaccharide-producing lactic acid bacterial strain for the production of high-molecular-mass heteropolysaccharides of at least $2.10^6$ Dalton during fermentation.

Interesting co-cultures according to the invention are those comprising a Streptococcus thermophilus strain according to the invention.

The invention relates to the use of Streptococcus thermophilus for the preparation of functional starter cultures and co-cultures in food fermentations.

Further, said functional starter cultures or co-cultures may be used for the fermentation of a food product, for instance said food product being a dairy product chosen from the group of milk products, fermented milk drinks, yoghurt, cheeses, sour cream, whipped toppings, quark and kefir.

The invention further relates to a dairy product obtainable by any of the methods of the invention.

According to an interesting embodiment of the invention, starter cultures producing EPS are promising for the production of low-fat Mozzarella cheese to enhance moisture retention. Therefore the invention more generally relates to any of the methods of the invention wherein *Streptococcus thermophilus* ST 111, for instance as a functional starter culture or as a co-culture, is used for the production of a Mozzarella cheese.

Also EPS may play an important role in the textural and sensorial quality of bread Another embodiment of the present invention relates to a functional starter culture for the fermentation of a yoghurt comprising a culture of the *Streptococcus thermophilus* ST 111 strain as herein defined and a culture of *Lactobacillus delbrueckii* subsp. *bulgaricus*.

However, it is contemplated that in cases where it is not possible to add the bacterial strain that produces the exopolysaccharide, such as *Streptococcus thermophilus* ST 111, itself to the starter culture or to the food product, isolated exopolysaccharide derived from or originating from *Streptococcus thermophilus* ST 111 can be used instead.

The invention thus relates to the use of the high-molecular-mass heteropolysaccharide as an additive in fermented as well as in non-fermented food products.

Therefore, the invention also relates to the use of a high-molecular-mass exopolysaccharide of at least $2.10^6$ Dalton obtained by or obtainable by any of the methods of the invention as an additive to fermented or non-fermented food. The production processes described herein allow for a high yield of said exopolysaccharides, for instance using the strains of the invention under the optimized culture conditions herein described. Moreover the EPS produced by the methods of the invention is very easy to isolate in a simple way providing highly pure product.

The exopolysaccharide can be applied as a "friendly" labeled additive in the production of any of the above-mentioned food products using processes familiar to those skilled in the art. The level of exopolysaccharide will generally be from 0.01 to 15%, wt/vol, more preferred from 0.1 to 10%, wt/vol, most preferred from 0.5 to 5%, wt/vol.

More specific, the invention relates to the use of a high-molecular-mass exopolysaccharide of at least $2.10^6$ Da obtained by or obtainable by any of the methods of the invention as an additive to a fermented or non-fermented food product for improving water retention of the food product, for instance for decreasing syneresis, or for improving the texture of said food product. Said food product may be chosen from the group of milk products, fermented milk drinks, yoghurt, cheeses, ice cream, soups, sour cream, whipped toppings, quark, kefir and sauces or chosen from the fermented products shown in Table 7.

The invention, now being generally described, will be more readily understood by reference to the following examples, which are included merely for purposes of illustration of certain aspects and embodiments of the present invention and are not intended to limit the invention.

BRIEF DESCRIPTION OF TABLES AND FIGURES

Table 1. Growth and exopolysaccharide production of *S. thermophilus* ST 111 in different media at 42° C. and free pH after 12 h of incubation.

Table 2. Influence of the medium composition on growth and EPS production for strain *S. thermophilus* ST 111; fermentations were performed at 37° C. and constant pH of 5.8.

Table 3. Influence of temperature on growth and EPS production for strain *S. thermophilus* ST 111; fermentations were performed in milk supplemented with 1.6% of lactalbumine hydrolysate, at a constant pH of 5.8.

Table 4. Influence of the pH value on growth and EPS production for strain *S. thermophilus* ST 111; fermentations were performed in milk supplemented with 1.6% of lactalbumine hydrolysate, at 42° C.

Table 5. Influence of a constant pH of the fermentation medium on the molecular mass of the EPS produced by *S. thermophilus* ST 111 in milk with lactalbumine hydrolysate (1.6%, m/v) at a constant temperature of 42° C. Because all molecular mass values were above $2.0 \times 10^6$ Da, the retention times of the corresponding peaks are reported. Sample times were linked to the amount of NaOH (10N) added to the fermentor. Two samples were collected after 12 h and 24 h of fermentation, respectively.

Table 6. The influence of sugar combinations on the fermentation parameters of *S. thermophilus* ST111 grown in milk medium.

Table 7. Fermented foods and their associated lactic acid bacteria

FIG. 1. Influence of temperature on the specific growth rate $\mu_{max}$ (in $h^{-1}$) of *S. thermophilus* ST111 in milk enriched with 1.6% (m/v) lactalbumine hydrolysate at a constant pH 5.8. The solid line is drawn according to the model (Rosso et al., 1995). Symbols represent the experimental data obtained by fermentations on 10 liter (■) and 100 ml scale (○).

Figure 2:
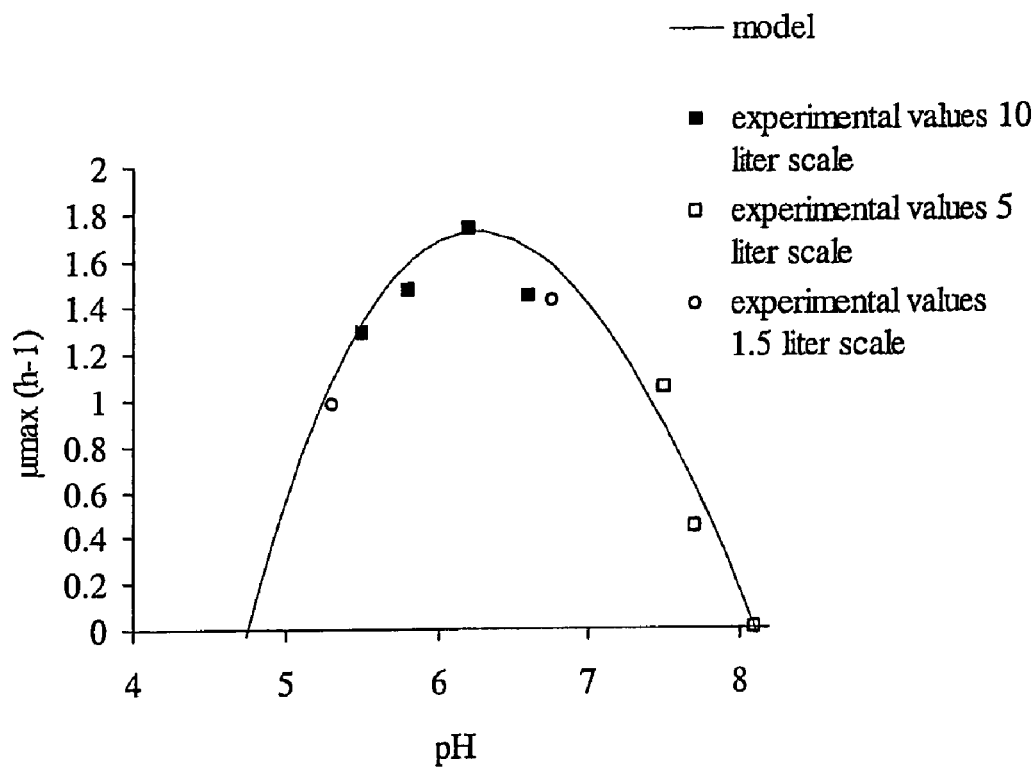

FIG. 2. Influence of pH on the specific growth rate $\mu_{max}$ (in $h^{-1}$) of *S. thermophilus* ST111 in milk enriched with 1.6% (m/v) lactalbumine hydrolysate at a constant temperature of 42° C. The solid line is drawn according to the model (Rosso et al., 1995). Symbols represent the experimental data obtained by fermentations on 10 liter (■), 5 liter (□) and 1.5 liter (○) scale.

FIG. 3. (A) Subunit structure of the exopolysaccharide produced by *S. thermophilus* ST111. (B) 400-MHz $^1$H-NMR spectrum of the EPS from *S. thermophilus* ST111.

Figure 4:
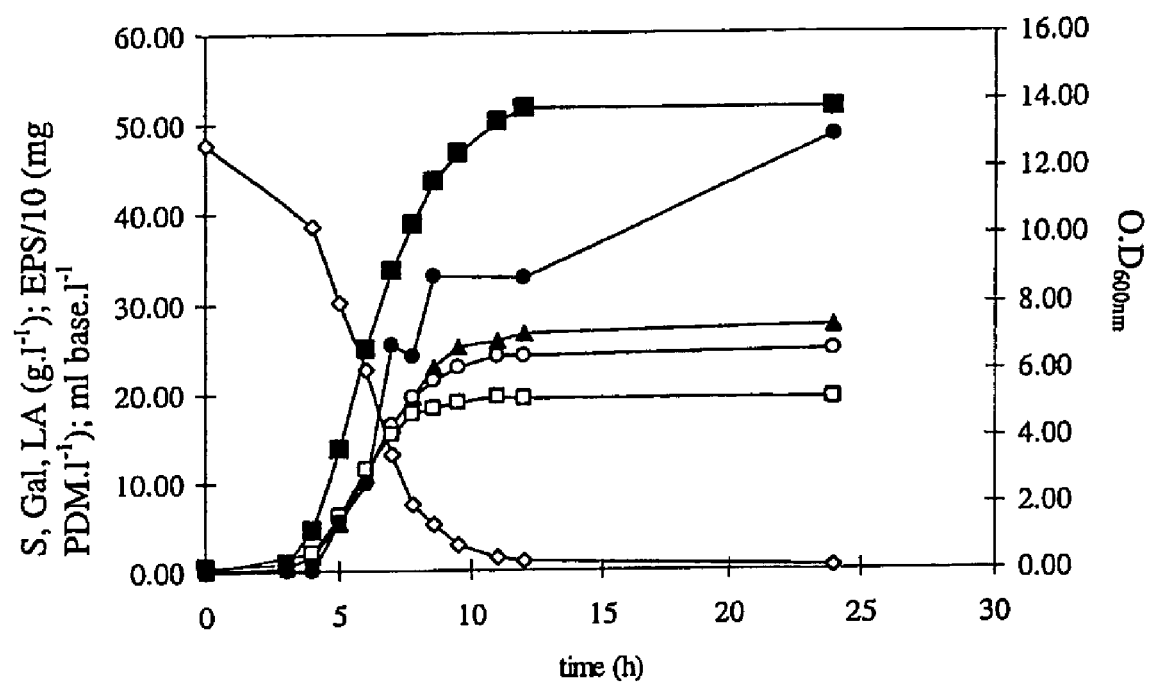

FIG. 4. Fermentation profile of *S. thermophilus* ST111 at a constant temperature of 37° C. and a constant pH of 5.8 in milk medium enriched with lactalbumine hydrolysate (10.0% skimmed milk powder and 1.6% lactalbumine hydrolysate, m/v). The experimental data are displayed: optical density at 600 nm (■), lactose (◇, g.l$^{-1}$), lactic acid (○, g.l$^{-1}$), galactose (□, g.l$^{-1}$), cumulative base consumption (▲, ml base.l$^{-1}$) and total exopolysaccharides (●, mg PDM.l$^{-1}$).

FIG. 5. Gel permeation chromatogram of EPS produced by *S. thermophilus* ST111 in milk medium (10.0%, m/v, skimmed milk powder) enriched with lactalbumine hydrolysate (1.6%, m/v) at pH 5.8 and 42° C. after 175 ml of base consumption. Vertical lines represent the molecular mass markers: (1) 1800 kDa, (2) 670 kDa, (3) 410 kDa, (4) 270 kDa, (5) 150 kDa, and (6) 80 kDa.

Figure 6A:
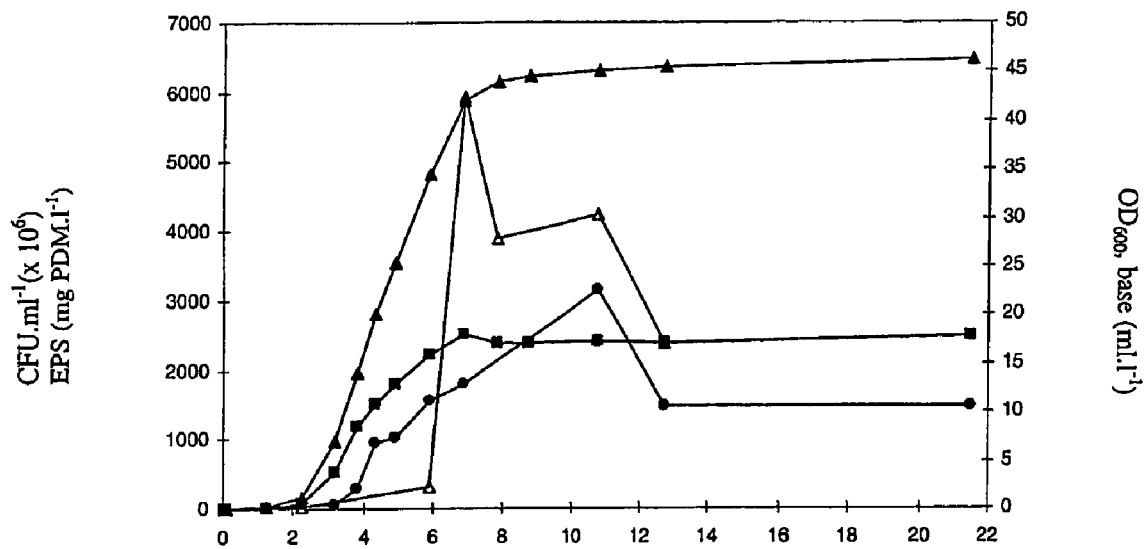
Figure 6B:
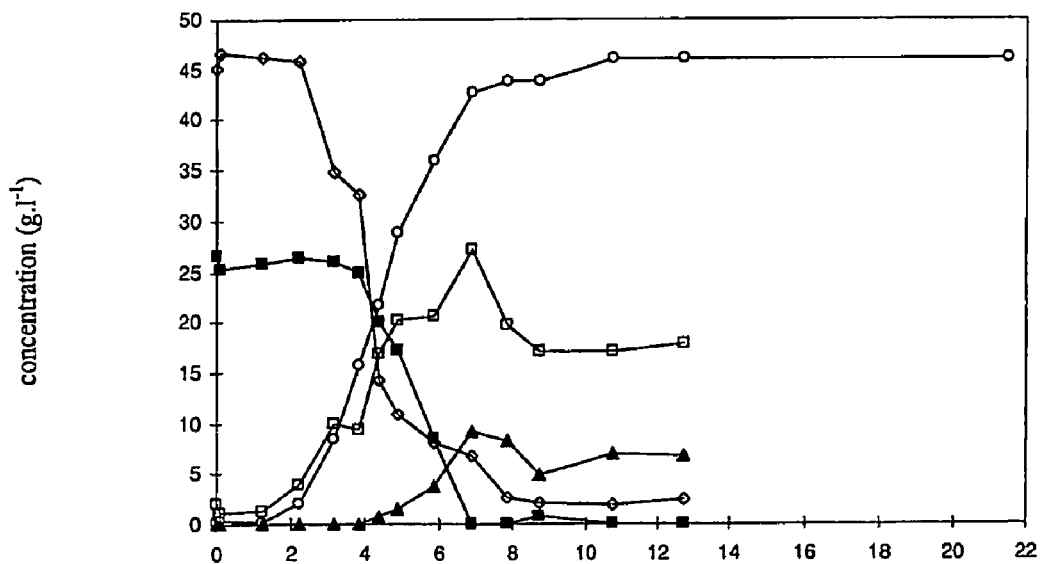

FIG. 6. Fermentation profiles of *S. thermophilus* ST111 grown in modified milk medium (10.0%, m/v skimmed milk powder and 1.6%, m/v lactalbumine hydrolysate) with addition of sucrose (2.5%, m/v). In part A optical density at 600 nm (●), colony forming units (Δ, CFU.ml$^{-1}$), cumulative base consumption (▲, ml base.l$^{-1}$) and total exopolysaccharides (◆, mg PDM.l$^{-1}$) are displayed. In part B lactose (◇, g.l$^{-1}$), lactic acid (○, g.l$^{-1}$), galactose (□, g.l$^{-1}$), sucrose (●, g.l$^{-1}$) and fructose (▲, g.l$^{-1}$) are displayed.

Figure 7:
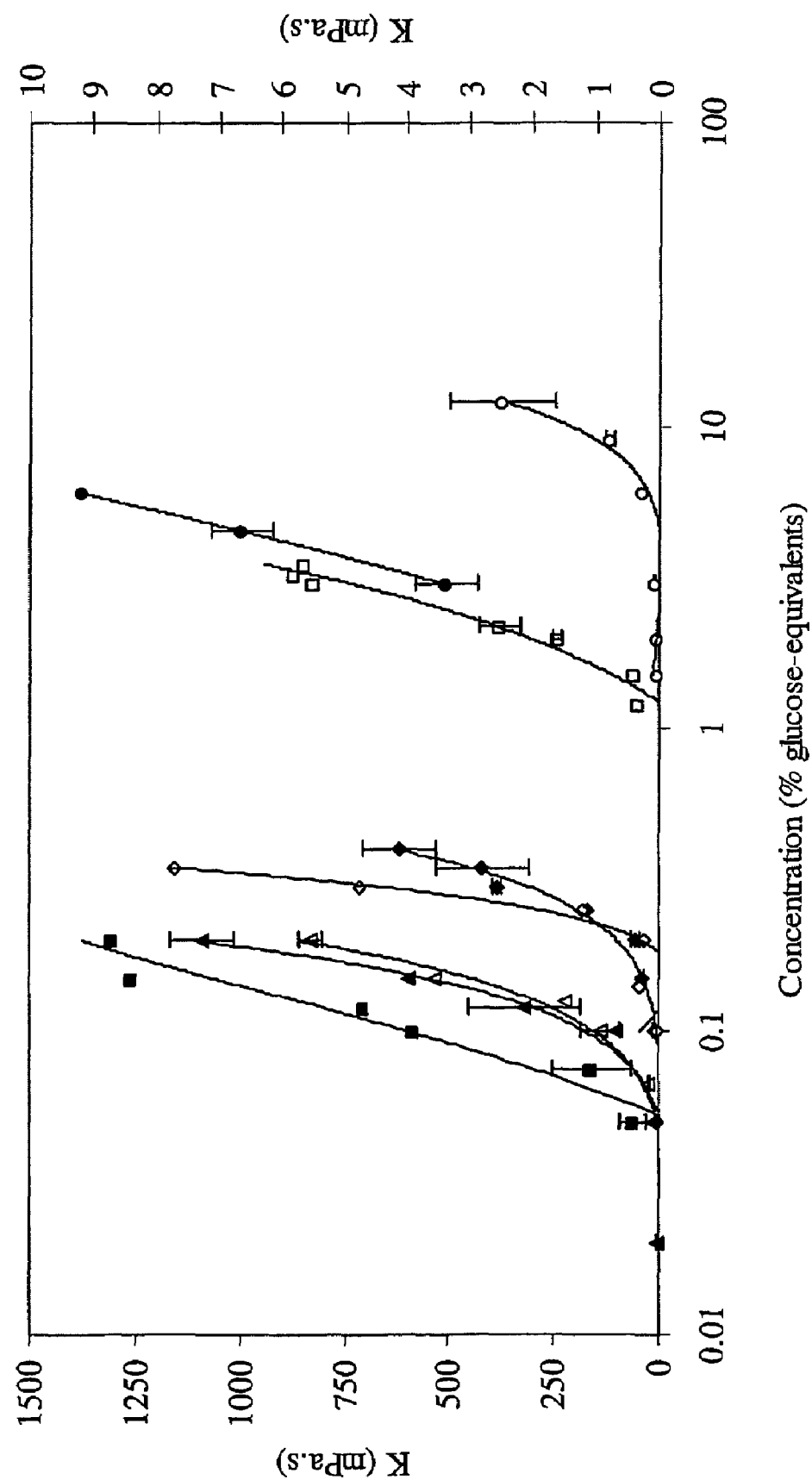

FIG. 7. The influence of different EPS concentrations on the consistencies (K) of the EPS solutions. Strains were grown in milk (10.0%, wt/vol, skimmed milk powder) supplemented with lactalbumine hydrolysate (1.6%, wt/vol) for 12 h at 42° C. and at a constant pH 6.2. Guar gum (●), non-floating EPS of *S. thermophilus* LY03 (▲), floating EPS of *S. thermophilus* LY03 (Δ), non-floating EPS of *S. thermophilus* ST 111 (◆), floating EPS of *S. thermophilus* ST 111 (◇), non-floating EPS of *S. thermophilus* ST 113 (□), non-floating EPS of *S. thermophilus* STD (●, second Y-axis), and non-floating EPS of *S. thermophilus* CH101 (○).

EXAMPLES

Example 1

Materials and Methods

Strain and Strain Propagation.

*Streptococcus thermophilus* ST 111 was used as the EPS-producing strain. The strain was disposed on May 29, 2002 under the accession number LMG P-21524 at the Belgian Coordinated Collections of Microorganisms (BCCM/LMG culture collection).

The strain was stored at −80° C. in de Man-Rogosa-Sharpe (MRS) medium (Oxoid, Basingstoke, United Kingdom). To obtain exponentially growing cultures, *S. thermophilus* ST 111 was propagated twice at 42° C. for 12 h in the medium identical to the one used for the fermentations later on.

Media

In MRS medium (de Man et al., 1960), M17 medium (Terzaghi & Sandine, 1975), and HJL medium (Stingele et al., 1996), lactose, sucrose, glucose, galactose, fructose, and rhamnose were first tested as the sole energy source (2.0%, m/v) for growth of *S. thermophilus* ST 111 on 10-ml scale. Then, different media were tested in Erlenmeyer flasks on 50-ml scale as to their capacity to support growth (measured by its final pH) and EPS production (measured as EPS yield) (Table 1).

For all fermentations on 10-l scale, milk medium (10% skimmed milk powder, m/v) was used. When the influence of the nitrogen source was tested, milk medium was supplemented with casitone (1.6%, m/v; Difco Laboratories), tryptone (1.6%, m/v; Oxoid) or lactalbumine hydrolysate (1.6%, m/v; Oxoid).

Fermentation Conditions, on Line Analysis and Sampling.

All fermentations were performed in an in situ sterilisable 15-l laboratory fermentor (Biostat C, B. Braun Biotech International, Melsungen, Germany) containing 10 l of milk medium. The milk medium was sterilised in the autoclave at 121° C. for 20 min, and aseptically pumped into the fermentor.

Off Line Analyses.

To measure the optical density the method described by Kanasaki et al. (1975) was used. Briefly, samples were diluted with 0.2% (m/v) EDTA, and 10 N NaOH was added to solubilise casein micelles. The optical density was measured at 600 nm ($OD_{600}$), using 0.2% EDTA as blanco. These measurements were done in duplicate. For the viable cell counts, an agar medium composed of 1.0% (wt/vol) yeast extract (VWR International), 1.5% (wt/vol) peptone (Oxoid), 1.0% (wt/vol) tryptone (Oxoid), 1.0% (wt/vol) glucose, 0.1% (vol/vol) Tween 80, and 1.5% agar (Oxoid), was used. EPS were isolated as described below; the yield was expressed as the amount of polymer dry mass (PDM) after drying at 42° C. for 48 h. Lactic acid and sugar concentrations were determined by high pressure liquid chromatography (HPLC) as described previously (De Vuyst et al., 1998). The maximum specific growth rate $\mu_{max}$ ($h^{-1}$) was calculated as the maximum slope from the linearised values of the optical density as a function of the fermentation time (h).

Isolation of EPS.

EPS were isolated according to the method of Degeest & De Vuyst (1999). Briefly, a trichloroacetic acid (TCA) and acetone precipitation were carried out consecutively twice, resulting in a floating and a pelleted EPS fraction. Usually, after the first acetone precipitation only a pelleted EPS fraction was detected, while after the second acetone precipitation both fractions were recovered. Both fractions were always collected and dried together. Due to the low solubility in water of the EPS, about 77±2% of the produced EPS were lost during the second TCA and acetone precipitation steps. For the EPS isolated at the beginning of the stationary phase (after 10 h of fermentation) and at the end of the fermentation (after 24 h), this loss was much lower, being about 62% and 45%, respectively. This was probably due to the fact that these EPS fractions were more soluble.

Example 2

Characterisation of EPS

Molecular Mass Determination of EPS

The EPS material isolated as described above was dissolved in MilliQ water (Millipore Corp., Bedford, Mass., USA), dialysed against distilled water at 4° C. for four days with water replacement twice a day, using Spectra/Por membranes (VWR International) with a MMCO of 3500 Da, and subsequently freeze-dried.

The molecular mass of the isolated EPS of all fermentations was determined by gel permeation chromatography. A Sephacryl S-400 gel (Amersham BioSciences AB, Uppsala, Sweden) was used. Samples containing about 50 mg.ml$^{-1}$ of lyophilised EPS were applied. The EPS were eluted with 50 mM potassium phosphate/NaOH buffer (pH 6.8) containing 0.15 M NaCl. A dextran standard series (molecular masses between $8.0 \times 10^4$ and $1.8 \times 10^6$ Da) was used to estimate the EPS molecular mass. The polysaccharide content was determined by on line refractive index detection (Waters refractive index detector, Waters Corp., Milford, Mass., USA).

For comparison of the molecular mass of the EPS material obtained from fermentations carried out at constant pH, differences in growth rate and acidification between these fermentation samples have to be eliminated. Therefore, sampling times to harvest EPS were linked to the amount of NaOH (10 N) added to the medium for pH control, namely after addition of 50, 100, and 175 ml. Two other samples were collected after 12 h and 24 h of fermentation, respectively. The EPS of these samples was not dried, but immediately dissolved in approximately 50 ml of milliQ water, followed by dialysis and lyophilisation. When the EPS produced by *S. thermophilus* ST 111 was present in high concentrations, it could easily be precipitated with acetone and recovered as a floating material from fermented milk medium. Gel permeation chromatography of this material resulted in a peak with a molecular mass of more than $2 \times 10^6$ Da (FIG. 5). If the amount of EPS was rather low, the floating material could be detected only after a second acetone precipitation step. When the strain was grown in MRS, M17, and HJL, the pelleted material was contaminated with polysaccharides derived from yeast extract and peptone.

Exopolysaccharide Structure Elucidation by One-Dimensional NMR Spectroscopy.

For structure determination, EPS material was obtained from fermentations carried out in milk medium, and isolated and dialysed as described above. The lyophilised polysaccharide was dissolved directly in $D_2O$ (99.9% D; Goss Scientific Instruments Ltd., Essex, United Kingdom). NMR spectra were recorded at a probe temperature of 70° C. The elevated temperature shifted the HOD signal to higher field into a clear region of the spectrum. The higher temperature also increased spectral resolution by reducing the sample viscosity. The NMR spectra were recorded on a Bruker Avance DPX400 MHz spectrometer operating with Z-field gradients and using Bruker's pulse programmes. Chemical shifts are expressed in ppm relative to internal acetone, δ 2.225. The 1D $^1$H spectra were processed with 32,768 data points. The 2D gs-DQF-COSY spectrum was recorded in magnitude mode at 70° C., the time-domain data was multiplied by a squared-sine-bell function (SSB 0). After applying linear-prediction and after Fourier transformation, data sets of 1024 by 1024 points were obtained.

Figure 3B:
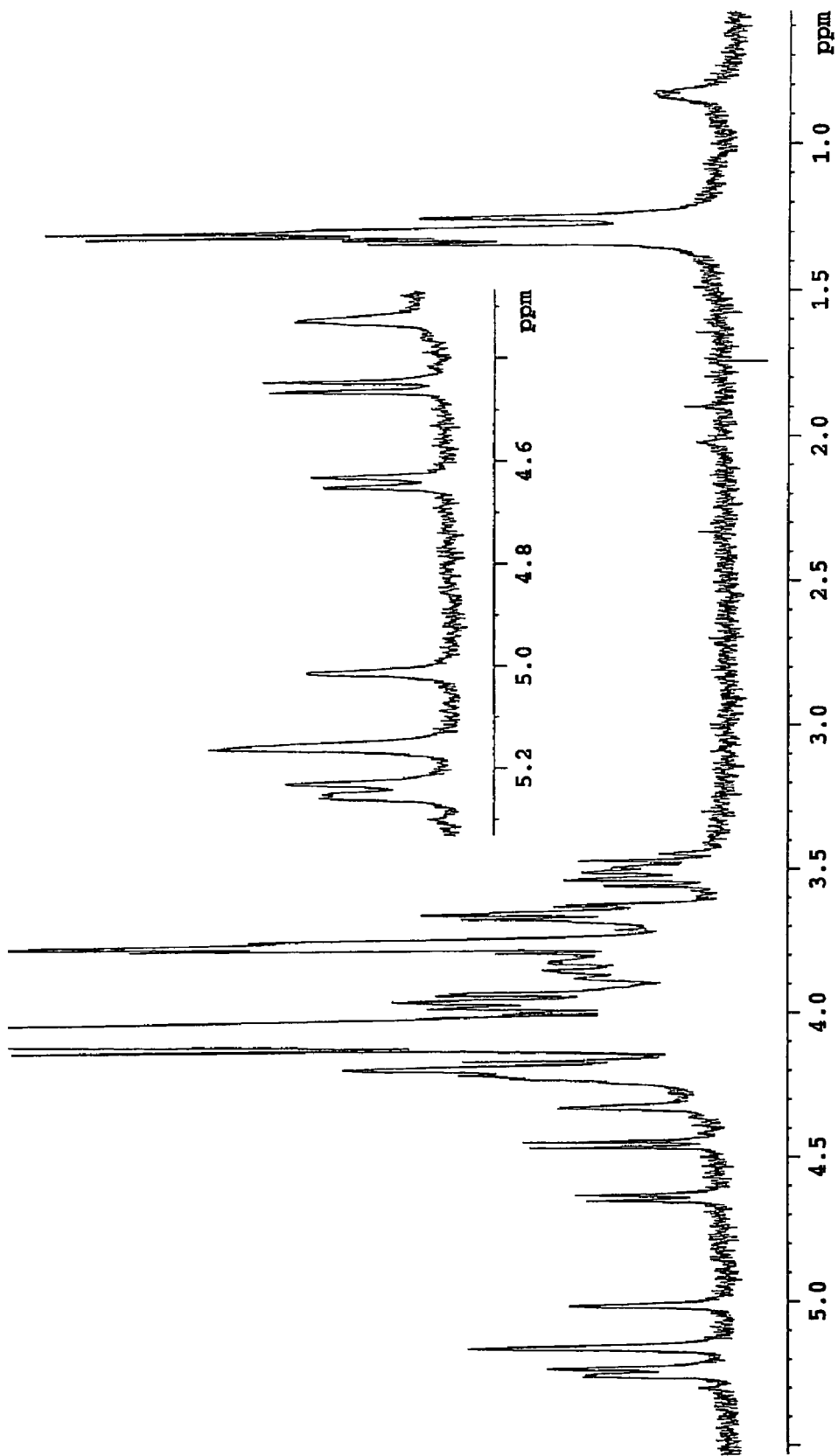

To determine the monomer composition of the EPS produced by *S. thermophilus* ST 111, a culture grown in milk medium at 42° C. and with free pH, was used. The monomer composition was determined after acid hydrolysis of purified EPS with 6 M trifluoroacetic acid (TFA) at 100° C. for 3 h, using an HPLC with pulsed amperometric detection (Dionex, Sunnyvale, Calif., USA) as described previously (Degeest et al., 2001a), giving a galactose/rhamnose ratio of 2.5:1.0. This composition was also confirmed by NMR spectroscopy. The $^1$H spectra recorded for the EPS samples, isolated during the stationary phase from several milk fermentations of *S. thermophilus* S111, were identical (FIG. 3). There were seven low field H-1 signals, designated A-G in FIG. 3 (δ 5.26 A H-1, 5.25 B H-1, 5.16 C H-1, 5.16 D H-1, 5.01 E H-1, 4.65 F H-1 and 4.45 GH-1). The locations of the related H-2 resonances were available from the COSY spectrum (δ 4.02 A H-2, 4.05 B H-2, 3.96 C H-2, 4.03 D H-2, 4.35 E H-2, 3.50 F H-2 and 3.53 G H-2). From this information, the polysaccharide repeating unit comprises two rhamnosyl and three α-galactosyl (A-E) linkages with two β-galactosyl linkages (F,G) displaying characteristic trans couplings (FIG. 3A). The spectra and the H-1 and H-2 chemical shifts resulted in the structure represented in FIG. 3B.

Example 3

Growth and Exopolysaccharide Production Kinetics of *S. thermophilus* ST 111

*S. thermophilus* ST 111 only grew in MRS, M17, and HJL media supplemented with glucose, lactose, and sucrose as the sole energy source. On 50-ml scale it was observed that EPS production was comparable in all three media when 2.0% of lactose was used, with an increase in EPS yield for higher lactose concentrations. In milk medium, both growth and EPS production were enhanced when an additional energy or nitrogen source were applied. Contaminating polysaccharide material from medium constituents was present in all complex media, except in milk (Table 1).

*S. thermophilus* ST 111 displayed a very low proteolytic activity, as indicated by its slow coagulation of milk at a suboptimal growth temperature of 30° C. Further, fermentation in milk alone with *S. thermophilus* ST 111 only slightly improved the viscosity of the medium. During fermentations performed in milk medium at 37° C. with pH control, *S. thermophilus* ST 111 produced about 70 mg of PDM (EPS) per liter after 12 h of fermentation (Table 2).

Example 4

Effect of Nitrogen Source on EPS Production

The influence of the nitrogen source was tested. Casitone, tryptone, and lactalbumine hydrolysate were sterilised separately and aseptically added to the fermentor. All these fermentations were performed at 37° C. and at a constant pH of 5.8.

To keep the fermentation medium homogeneous, agitation was performed at 100 rpm with a stirrer composed of three standard impellers. The fermentor was inoculated with 1.0% (v/v) of an exponentially growing culture of the ST 111 strain. The temperature, pH, and agitation were computer-controlled and monitored on line (Micro MFCS for Windows™NT software, B. Braun Biotech International). At regular time intervals, samples were aseptically withdrawn from the fermentor to determine the optical density, number of viable cells (CFU/ml), EPS yield, and lactic acid, galactose, and residual lactose concentrations.

A fermentation profile for the growth in milk supplemented with 1.6% of lactalbumine hydrolysate is given in FIG. 4. Growth was very fast ($\mu_{max}$=1.38 h$^{-1}$) with a short lag phase, followed by an exponential growth phase that stopped after complete lactose consumption. The EPS production paralleled the exponential growth phase, and continued during the stationary phase. The increase at the end of the stationary phase was probably due to the fact that less material was lost upon isolation due to its better solubility.

When milk medium was enriched with tryptone, casitone, or lactalbumine hydrolysate, both growth and EPS production were enhanced (Table 2).

In the presence of lactalbumine hydrolysate and tryptone, the growth profile and the EPS production were similar, but in the presence of casitone the $\mu_{max}$ was lower as well as the maximum EPS yield (Table 2). For further fermentation studies, lactalbumine hydrolysate was used to supplement the milk because this medium supported the highest maximum specific growth rate, which is important for the growth-associated EPS production. Also, contaminating polysaccharides are lacking in this medium.

Example 5

Effect of Temperature on EPS Production

Fermentations were carried out in milk medium supplemented with lactalbumine hydrolysate (1.6%) at a temperature of 25° C., 32° C., 37° C., 42° C., 46° C. and 49° C., all performed at a constant pH of 5.8.

To determine the critical temperature for growth, static 100-ml fermentations in milk were performed at temperatures below 25° C. and above 46° C. The influence of temperature on $\mu_{max}$ was modeled according to the equations of Rosso et al. (1995).

The results of the influence of the fermentation temperature on growth and EPS production by *S. thermophilus* ST 111 are given in Table 3. The strain showed very good growth within the temperature range from 32 to 46° C. (the maximum specific growth rate varied from 1.13 h$^{-1}$ to 1.46 h$^{-1}$), and a slower growth at 25° C. ($\mu_{max}$=0.40 h$^{-1}$) and 49° C. ($\mu_{max}$=0.70 h$^{-1}$). The optimal growth temperature was 42° C. ($\mu_{max}$=1.46 h$^{-1}$). A very slow growth was detected at 20° C. (final pH=4.7) and 50° C. (final pH=5.4), but no growth was observed at 15° C. and 55° C. The minimum (17° C.), optimum (40° C.) and maximum (52° C.) temperature were modeled with the equation of Rosso (1995) (FIG. 1). The activation energy of growth ($E_a$) was calculated as 46 kJ.mol$^{-1}$ (Arrhenius plot not shown). The highest EPS production was detected when the strain was grown at 37 and 42° C., namely 485 and 423 mg of PDM.l$^{-1}$. It was much lower at 25 and 46° C., namely 294 and 176 mg of PDM.l$^{-1}$, respectively (Table 3). Although the relatively small maximum growth rate at 49° C. (maximum OD$_{600}$ =3.4), the EPS production was rather high (152 mg of PDM.l$^{-1}$), indicating a higher specific EPS production at this temperature.

At different temperatures the EPS production displayed the same profile for all fermentations, except for the ones carried out at 25 and 32° C. The EPS concentration at the end of the growth phase was similar for fermentations at 37° C. (327 mg PDM.l$^{-1}$) and 42° C. (305 mg PDM.l$^{-1}$). At lower temperatures, the EPS yields decreased at the end of the fermentation.

Example 6

Effect of pH on EPS Production

The fermentation temperature was kept constant at 42° C., and the initial pH of the milk was adjusted to pH 5.1, 5.5, 5.8, 6.2, or 6.6, and kept constant by automatic addition of 10 N NaOH.

Another series of fermentations was carried out at 42° C. and at constant pH values of pH 5.3, 6.7, 7.5, 7.7, 8.1 and 8.7, to determine the critical pH values for growth. The influence of pH on $\mu_{max}$ was modeled according to the equations of Rosso et al. (1995).

Because of the low EPS amounts isolated from milk fermented with *S. thermophilus* ST 111 without pH control, several fermentations were carried out at different constant pH values (Table 4). They were all performed at 42° C., the temperature used for the production of yoghurt, and because this temperature resulted in the fastest growth (Table 3). The highest maximum growth rate was detected when the pH was kept constant at pH 6.2 during fermentation. The $\mu_{max}$ for this fermentation was 1.79 h$^{-1}$ and the maximum OD$_{600}$ value was highest as well (13.8). The highest EPS yield (556 mg of PDM/l) was detected when strain ST 111 was grown at 42° C. and at a constant pH of 6.2. At constant pH 5.5, growth was much slower ($\mu_{max}$=1.28 h$^{-1}$) and EPS production was lower (215 mg of PDM/l). At constant pH 5.1, growth was even more slow ($\mu_{max}$=1.04 h$^{-1}$) and EPS production was lowest (101 mg of PDM/l). Applying the equation of Rosso, the optimal pH for the growth of this strain was estimated to be pH 6.25 with a $\mu_{max}$ of 1.78 h$^{-1}$ (FIG. 2). No growth could be detected below pH 4.8 (pH$_{min}$) and above pH 8.1 (pH$_{max}$).

Example 7

Influence of the Growth Conditions on the EPS Monomer Composition and Molecular Mass EPS material collected from different fermentations was used for molecular mass determination and monomer composition analyses. Growth conditions (milk with different nitrogen sources, temperature, and pH) did not affect the monomer composition of the EPS produced by *S. thermophilus* ST 111. The same composition of 5 Gal and 2 Rha was determined for all samples analyzed. Also, the molecular mass of the EPS was not influenced by the growth conditions and sampling time (Table 5). All GPC chromatograms showed the presence of high-molecular-mass EPS (>2000 kDa) (FIG. 5). For all fermentations no second, low-molecular-mass peak appeared in function of time, indicating the production of a stable EPS under the different conditions.

Example 8

Influence of Sugar Combinations on the Growth and EPS Production of *S. thermophilus* ST 111

All fermentations were carried out in a 10 l (working volume) Biostat® C fermentor (B. Braun Biotech, Melsungen, Germany). The fermentations were done in enriched milk medium (10.0% skimmed milk powder and 1.6% lactalbumine hydrolysate, m/v) to which an additional sugar (2.5%, m/v) was added (glucose, galactose, fructose, or sucrose). This modified milk medium has the advantage to enhance the bacterial growth and EPS production without the interference of medium components with the isolation of EPS. All fermentations were pH and temperature controlled (pH 6.2, T=42° C.). Bacterial growth was followed by measuring the base consumption (on line), the optical density (OD) at 600 nm, and cell counts (CFU per ml) after plating on an agar medium described before in Example 1. The measurements of OD in milk were done in duplicate and averaged according to a modified method of Kanasaki et al. (1975). The EPS were isolated from 500 ml samples using the isolation protocol described in Example 1. Floating and non-floating EPS material were collected separately. At regular times, samples were taken for analysis of residual sugars and produced metabolites by HPLC with a refraction detector (Waters Corporation, Milford, Mass., USA). In the case of fermentations with fructose or sucrose as additional carbohydrate source, the concentrations of fructose, galactose, lactose, and sucrose were determined using an HPLC with amperometric detection (Dionex, Sunnyvale, Calif., USA). The results are presented in Table 6 and FIG. 6. Bacterial growth and EPS concentration were highest when glucose or sucrose was added to the enriched milk medium. When sucrose was used as an additional carbohydrate source, an exceptional amount of more than 3 g of polymer dry mass (PDM) of EPS per liter medium could be recovered (Table 6). The lowest EPS concentration was found in the case of galactose. In this experiment no distinction was made between floating and non-floating material during EPS Isolation. Separate collection of both EPS fractions usually resulted in higher yields as can be seen in the case of glucose. An EPS collection without making a distinction between floating and non-floating EPS material resulted in an EPS concentration that was 53% lower than when both fractions were isolated and collected separately (Table 6). This loss of EPS could be attributed to the lower solubility of the high EPS concentrations. The carbohydrate source did not change the specific EPS yield (Table 6). Glucose was consumed more slowly than lactose while sucrose and lactose were consumed simultaneously (FIG. 6). When glucose or sucrose were added to the milk medium, the yield of lactic acid based on the lactose consumption ($Y_{LA/S}$) was higher when compared to milk medium with no sugar addition. *S. thermophilus* ST 111 consumed sucrose, most probably by splitting sucrose into fructose and glucose. Glucose is then consumed, yielding two extra moles of lactic acid. Compared to the theoretical value ($Y_{Fru/Suc}$=1.0 mol of fructose per mol of sucrose), the yield of fructose based on the consumption of sucrose is small ($Y_{Fru/Suc}$=0.4 mol of fructose per mol of sucrose). A limited amount of fructose is secreted into the medium (Table 1).) which indicates that part of the fructose has been used for EPS formation. In milk medium, galactose and fructose were consumed in a very little amount by *S. thermophilus* ST 111. When galactose was added, the yield of galactose based on the consumption of lactose ($Y_{Gal/S}$=0.66 mol of galactose secreted per mol of lactose consumed) was lower compared to the theoretical value ($Y_{Gal/S}$=1 mol of galactose secreted per mol of lactose consumed) when no galactose would have been consumed (Table 6). This indicates a limited galactose metabolism of *S. thermophilus* ST 111. The fructose consumption in combination with lactose was rather slow and limited (35% of the initial fructose is consumed after 24 h of fermentation) and lead to a small increase in the yield of lactic acid based on the consumption of lactose ($Y_{LA/S}$=2.15 mol of lactic acid per mol of lactose) compared to the theoretical value ($Y_{LA/S}$=2.00 mol/mol).

Example 9

Characterization of EPS: Apparent Viscosity Measurements of Pure EPS Solutions

Strains and Strain Propagation

The EPS-producing strains *S. thermophilus* LY03, *S. thermophilus* ST 113, *S. thermophilus* STD, and *S. thermophilus* CH101 were propagated in the same way as *S. thermophilus* ST 111 and these strains were included to compare the viscosifying effect of their EPS with that from *S. thermophilus* ST 111.

Methods

To study and compare the rheology of pure EPS solutions from *S. thermophilus* ST 111 with those from four other EPS-producing *S. thermophilus* strains (*S. thermophilus* LY03, *S. thermophilus* ST 113, *S. thermophilus* STD, and *S. thermophilus* CH101), fermentations were carried out in milk medium supplemented with lactalbumine hydrolysate (1.6%, wt/vol) to obtain EPS free of contaminating polysaccharides. After 12 h of fermentation at 42° C. and a constant pH of 6.2 (controlled by automatic addition of 10 N NaOH), EPS were isolated according to the method of Degeest & De Vuyst (1999). Likewise, a distinction was made between floating and non-floating EPS material. The two fractions were separately harvested, purified and analysed. Purification of the EPS was done according to the method mentioned above (example 2, molecular mass determination of EPS). Apparent viscosity measurements were performed on 0.5 ml samples, using a cone-plate Brookfield Digital Rheometer Model DV III (Brookfield Engineering Laboratories Inc., Stoughton, Mass., USA). The rheometer was equipped with a flat spindle, type CP 40 (Brookfield Engineering Laboratories Inc.), which rotated in a sample-containing chamber connected to a temperature-controlled cryostat water bath (Thermomix®, B. Braun Biotech International). The rheometer was controlled with the Brookfield Rheocalc software (Brookfield Engineering Laboratories Inc.). To study the rheology of solutions of purified EPS, a series of apparent viscosity measurements (during 90 s) were performed on solutions with varying EPS concentrations (expressed as glucose equivalents; Scott & Melvin, 1953) to determine the range of possible programmable measurements, that is a range were the torque was comprised between 15% and 85% of the maximum torque. It turned out that the different EPS solutions could not be compared at a common concentration. Subsequently, for each EPS flow curves were determined in a certain concentration range, depending on the EPS used. This has been performed by gradually increasing the velocity of the spindle with a constant step after a constant time interval (90 s). If possible, measurements were programmed to build flow curves composed of 10 to 20 experimental points. To compare the viscosity of the EPS from the different strains, the flow properties of these EPS solutions were determined by the power law model (Walter, 1998) given by $$\tau = K\gamma^v \quad (1)$$

for which $\tau$ is the applied shear stress (Pa), K is the consistency index (Pa·s) that is typical for a certain liquid, $\gamma$ is the velocity gradient or the so-called shear rate (s$^{-1}$), and v is an exponent that characterizes the shear-thinning (0<v<1) or shear-thickening (v>1) behaviour of a liquid. When v=1, the solution behaves as a Newtonian liquid. The different parameters of the power law equation are graphically obtained after linearisation of equation (1). The values of the parameters are independent of the applied shear rates and allow the comparison of different samples. Likewise, the consistency of an EPS solution was determined for different concentrations, based on flow curves measurements (see above). This resulted in a graphical presentation of the viscosifying effect of each EPS as a function of its concentration. Guar gum (from the leguminous plant *Cyamopsis tetragonolobus*; molecular mass approximately 220 kDa; Sigma, St. Louis, Mo., USA) *tetragonolobus*; molecular mass approximately 220 kDa; Sigma, St. Louis, Mo., USA) was used as a reference polysaccharide during all experiments. For each polysaccharide, programmable measurements were performed in triplicate for at least two different EPS concentrations. The parameters were averaged and standard deviations were calculated. All the flow curves were measured at 25° C.

Results

Flow curves were determined using different concentrations of pure EPS derived from the five strains mentioned above. The effect of the EPS concentration on the consistency (K, in mPa·s) of the different EPS solutions is given in FIG. 7. In general, K increased with increasing EPS concentration. However, large differences in the viscosifying effects of the different EPS were determined (FIG. 7). The highest consistencies were found for guar gum, EPS from *S. thermophilus* LY03, and EPS from *S. thermophilus* ST 111. A tenfold increase in concentration resulted in a similar range of K for EPS solutions from *S. thermophilus* ST 113. A high concentration of EPS from *S. thermophilus* STD displayed a very low-range consistency (9 mPa·s). No differences were observed between floating and non-floating EPS material of *S. thermophilus* LY03. In contrast, non-floating EPS from *S. thermophilus* ST 111 showed a different, lower K compared with the floating EPS material. Hence, *S. thermophilus* ST 111 possibly produces two high-molecular-mass EPS with different molecular masses, but which could not be differentiated experimentally from each other because these molecular masses exceeded the linear range of the gel permeation chromatography column. All different EPS discussed here displayed a shear-thinning character (0<v<1).

TABLE 1

|  | Milk medium | Enriched milk medium[‡] | Milk medium + 1.0% casamino acids | Milk medium + 4.0% sucrose | MRS with 2.0% lactose | HJL 2.0% lactose | HJL 4.0% lactose | HJL 8.0% lactose | HJL 4.0% sucrose | M17 0.5% lactose | M17 2.0% lactose | M17 4.0% lactose |
|---|---|---|---|---|---|---|---|---|---|---|---|---|
| Final pH | 4.6 | 4.3 | 3.8 | 3.8 | nd | nd | 4.2 | 4.3 | 4.2 | 5.0 | 4.5 | 4.5 |
| EPS yield[†] | 50 | 109 | 95 | 82 | 86 | 108 | 148 | 192 | 90 | 0 | 96 | 120 |

[‡]Enriched milk medium is composed of 10.0% (m/v) skimmed milk powder, 1.0% (m/v) bacteriological peptone, and 0.5% (m/v) yeast extract (De Vuyst et al., 1998).
[†]The EPS yield is expressed in mg polymer dry mass per liter. Results are given after subtraction of the EPS yield from the blanco medium (approximately 130 mg · l$^{-1}$ for enriched milk medium, 120 mg · l$^{-1}$ for MRS medium, 300 mg · l$^{-1}$ for HJL medium, and 350 mg · l$^{-1}$ for M17 medium).
nd = not determined.

TABLE 2

| Milk medium | Maximum OD$_{600}$ | Maximum cell number (CFU/ml) | $\mu_{max}$ (h$^{-1}$) | Maximum EPS yield (mg PDM/l) |
|---|---|---|---|---|
| without additional nitrogen source | 1.8 | $2.6 \times 10^9$ | 1.32 | 70 |
| with 1.6% (m/v) casitone | 10.4 | $2.4 \times 10^{10}$ | 0.92 | 254 |
| with 1.6% (m/v) tryptone | 10.7 | $4.5 \times 10^{10}$ | 1.22 | 580 |
| with 1.6% (m/v) lactalbumin hydrolysate | 13.8 | $8.0 \times 10^{10}$ | 1.38 | 485 |

TABLE 3

| Growth temperature (° C.) | Maximum OD$_{600}$ | Maximum cell number | $\mu_{max}$ (h$^{-1}$) | Maximum EPS yield (mg PDM/l) |
|---|---|---|---|---|
| 25 | 8.1 | $2.6 \times 10^9$ | 0.40 | 294 |
| 32 | 13.1 | $4.5 \times 10^9$ | 1.13 | 446 |
| 37 | 13.8 | $8.0 \times 10^{10}$ | 1.38 | 485 |
| 42 | 12.2 | $2.7 \times 10^9$ | 1.46 | 423 |
| 46 | 9.4 | $9.3 \times 10^8$ | 1.16 | 176 |
| 49 | 3.4 | $7.5 \times 10^8$ | 0.70 | 152 |

TABLE 4

| pH | Maximum O.D. $_{600\,nm}$ | Maximum cell number | $\mu_{max}$ (h$^{-1}$) | Maximum EPS yield (mg PDM/l) |
|---|---|---|---|---|
| 5.1 | 5.9 | $9.0 \times 10^8$ | 1.04 | 101 |
| 5.5 | 10.8 | $1.2 \times 10^9$ | 1.28 | 215 |
| 5.8 | 13.8 | $8 \times 10^{10}$ | 1.38 | 485 |
| 6.2 | 13.8 | $6.2 \times 10^9$ | 1.79 | 556 |
| 6.6 | 9.85 | $2.3 \times 10^9$ | 1.44 | 443 |

TABLE 5

| Constant pH value | Sampling time | | | | |
|---|---|---|---|---|---|
|  | 50 ml | 100 ml | 175 ml | 12 h | 24 h |
|  | Retention time (min) | | | | |
| pH 5.5 | 78.7 | 77.8 | 78.8 | 77.9 | 78.3 |
| pH 5.8 | 75.6 | 75.0 | 74.9 | 77.5 | 79.6 |
| pH 6.2 | 73.4 | 73.9 | 76.5 | 74.9 | 75.9 |
| pH 6.6 | 78.5 | 78.0 | 78.1 | 78.2 | 78.1 |

TABLE 6

| [a]Fermentation | $\mu_{max}$ (h$^{-1}$) | [d]OD$_{max}$ | Colony Forming Units (×10$^7$ CFU/ml) | [e]Total EPS$_{max}$ (mg PDM · l$^{-1}$) | [g]Y$_{P/S}$ (cmol/cmol) | [j]Y$_{LA/S}$ (mol/mol) | [k]Y$_{Gal/S}$ (mol/mol) | [l]Y$_{Fru/Suc}$ (mol/mol) | [m]Y$_{EPS/OD}$ (mg PDM/OD · l$^{-1}$) |
|---|---|---|---|---|---|---|---|---|---|
| 10% [b]SMP + 1.6% [c]LH + 2.5% glucose | 1.9 (0.99) | 16.0 | 517 | 1832 | [h]0.99 (0.99) | 2.50 (0.99) | 0.92 (0.99) | — | 104 (0.98) |
|  |  |  |  | [f]846 | [i]0.89 (0.99) |  |  |  | [f]20 (0.97) |
| 10% [b]SMP + 1.6% [c]LH + 2.5% galactose | 1.9 (0.99) | 12.1 | 43 | [f]495 | 0.85 (0.99) | 1.95 (0.99) | 0.66 (0.99) | — | [f]20 (0.97) |
| 10% [b]SMP + 1.6% [c]LH + 2.5% fructose | 1.6 (0.99) | 14.7 | 275 | 1248 | 0.98 (0.99) | 2.15 (0.99) | 0.89 (0.99) | — | 101 (0.99) |

TABLE 6-continued

| $^a$Fermentation | $\mu_{max}$ (h$^{-1}$) | $^d$OD$_{max}$ | Colony Forming Units (×10$^7$ CFU/ml) | $^e$Total EPS$_{max}$ (mg PDM · l$^{-1}$) | $^g$Y$_{P/S}$ (cmol/cmol) | $^j$Y$_{LA/S}$ (mol/mol) | $^k$Y$_{Gal/S}$ (mol/mol) | $^l$Y$_{Fru/Suc}$ (mol/mol) | $^m$Y$_{EPS/OD}$ (mg PDM/ OD · l$^{-1}$) |
|---|---|---|---|---|---|---|---|---|---|
| 10% $^b$SMP + 1.6% $^c$LH + 2.5% sucrose | 1.9 (0.99) | 18.0 | 595 | 3145 | 1.02 (0.99) | 4.10 (0.99) | 1.00 (0.98) | 0.41 (0.98) | 98 (0.97) |

$^a$Fermentations were done at pH 6.2 and 42° C.;
$^b$SMP = skimmed milk powder;
$^c$LH = lactalbumine hydrolysate;
$^d$OD = optical density at 600 nm;
$^e$Total EPS$_{max}$ = maximum total EPS concentration (floating + non-floating) in mg polymer dry mass per liter;
$^f$EPS isolated without differentiating between floating and non-floating EPS material;
$^g$Y$_{P/S}$ = yield of metabolite production (lactic acid, galactose, fructose) based on the consumption of the sugar source (lactose, glucose, sucrose, fructose);
$^h$yield calculated on the production of lactic acid and galactose based on the consumption of glucose and lactose in the growth phase;
$^i$yield calculated on the production of lactic acid based on the consumption of glucose and galactose in the stationary phase;
$^j$Y$_{LA/S}$ = yield of lactic acid based on lactose consumption;
$^k$Y$_{Gal/S}$ = yield of galactose based on lactose consumption;
$^l$Y$_{Fru/Suc}$ = yield of fructose based on the consumption of sucrose;
$^m$Y$_{EPS/OD}$ = specific EPS-yield.
The correlation coefficient r$^2$ is the value between round brackets and was obtained by linear regression

TABLE 7

| Type of fermented product | Lactid acid bacteria* |
|---|---|
| dairy products | |
| hard cheeses without eyes | L. lactis subsp. lactis, L. lactis subsp. cremoris |
| cheeses with small eyes | L. lactis subsp. lactis, L. lactis subsp. lactis var. diacetylactis, L. lactis subsp. cremoris, Leuc. mesenteroides subsp. cremoris |
| Swiss- and Italian-type cheeses | Lb. delbrueckii subsp. lactis, Lb. helveticus, Lb. casei, Lb. delbrueckii subsp. bulgaricus, S. thermophilus |
| butter and buttermilk | L. lactis subsp. lactis, L. lactis subsp. lactis var. diacetylactis, L. lactis subsp. cremoris Leuc. mesenteroides subsp. cremoris |
| yoghurt | Lb. delbrueckii subsp. bulgaricus, S. thermophilus |
| fermented, probiotic milk | Lb. casei, Lb. acidophilus, Lb. rhamnosus, Lb. johnsonii, B. animalis, B. bifidum, B. breve |
| kefir | Lb. kefir, Lb. kefiranofacies, Lb. brevis |

*B. = Bifidobacterium, L. = Lactococcus, Lb. = Lactobacillus, Leuc. = Leuconostoc

REFERENCES

Cerning, J. 1990. Exocellular polysaccharides produced by lactic acid bacteria. FEMS Microbiol. Rev. 87:113-130.

Cerning, J. 1995. Production of exopolysaccharides by lactic acid bacteria and dairy propionibacteria. Lait 75:463-472.

Degeest, B., and L. De Vuyst. 1999. Indication that the nitrogen source influences both amount and size of exopolysaccharides produced by Streptococcus thermophilus LY03 and modeling of bacterial growth and exopolysaccharide production in a complex medium. App. Environ. Microbiol. 65: 2863-2870.

Degeest, B., B. Janssens, and L. De Vuyst. 2001a. Exopolysaccharide (EPS) biosynthesis by Lactobacillus sakei O-1: production kinetics, enzyme activities, and EPS yields. J. Appl. Microbiol. 91:470-477.

Degeest, B., F. Vaningelgem, and L. De Vuyst. 2001b. Microbial physiology, fermentation kinetics, and process engineering of heteropolysaccharides from lactic acid bacteria. Int. Dairy J. 11:747-757.

de Man, J. C., M. Rogosa, and M. E. Sharpe. 1960. A medium for the cultivation of lactobacilli. J. Appl. Bacteriol. 23:130-135.

De Vuyst, L., and B. Degeest. 1999. Heteropolysaccharides from lactic acid bacteria. FEMS Microbiol. Rev. 23:153-177.

De Vuyst, L., F. Vanderveken, S. Van de Ven, and B. Degeest. 1998. Production by and isolation of exopolysaccharides from Streptococcus thermophilus grown in a milk medium and evidence for their growth-associated biosynthesis. J. Appl. Microbiol. 84:1059-1068.

De Vuyst, L., F. De Vin, F. Vaningelgem and B. Degeest 2001. Recent developments in the biosynthesis and applications of heteropolysaccharides from lactic acid bacteria. Int. Dairy J. 11: 687-707.

Faber, E. J., D. J. van Haaster, J. P. Kamerling, and J. F. G. Vliegenthart. 2002. Characterization of the exopolysaccharide produced by Streptococcus thermophilus 8S containing an open chain nononic acid. Eur. J. Biochem. 269: 5590-5598.

Kanasaki, M., S. Breheny, A. J. Hillier, and G. R. Jago. 1975. Effect of temperature on the growth and acid production of lactic acid bacteria. 1. A rapid method for the estimation of bacterial populations in milk. Aust. J. Dairy Technol. 30:142-144.

Monsan, P., S. Bozonnet, C. Albenne, G. Joucla, R. M. Willemot, and M. Remaud-Siméon 2001. Homopolysaccharides from lactic acid bacteria. Int. Dairy J. 11:675-685.

Rosso, L., J. R. Lobry, S. Bajard, and J. P. Flandrois. 1995. Convenient model to describe the combined effects of temperature and pH on microbial growth. Appl. Environ. Microbiol. 61:610-616.

Scott, T. A., and E. H. Melvin. 1953. Determination of dextran with anthrone. Anal. Chem. 25:1656-1661.

Stingele, F., J.-R. Neeser, and B. Mollet. 1996. Identification and characterization of the eps (exopolysaccharide) gene cluster from *Streptococcus thermophilus* Sfi6. J. Bacteriol. 178:1680-1690.

Terzaghi, B. E., and W. E. Sandine. 1975. Improved medium for lactic streptococci and their bacteriophages. *Appl Environ. Microbiol.* 29: 807-813.

Walter, R. H., 1998. Concentration regimes and mathematical modeling, p. 71-100. In Walter R. H. (ed.), Polysaccharide dispersions: chemistry and technology in food. Academic Press, London United Kingdom.

The invention claimed is:

1. *Streptococcus thermophilus* ST 111 strain, as deposited on May 29, 2002 under the accession number LMG P-21524 that produces exopolysaccharide which is a polymer of heptasaccharide units, which units have the following structure:

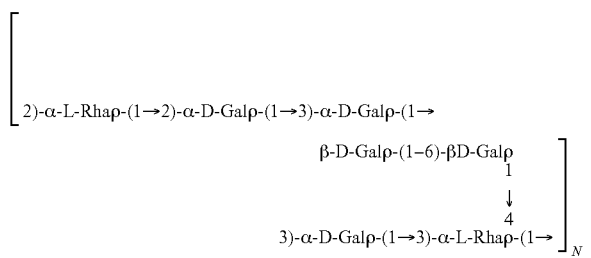

and having a molecular mass of at least $5 \times 10^6$ Daltons.

2. A functional starter culture comprising the exopolysaccharide-producing lactic acid bacterial strain of claim 1.

3. A co-culture comprising the exopolysaccharide-producing lactic acid bacterial strain of claim 1.

4. A method of producing high-molecular-mass heteropolysaccharides of at least $5 \times 10^6$ Daltons during fermentation comprising fermenting the functional starter culture according to claim 2.

5. A method of fermentation of a food product comprising adding the functional starter culture according to claim 2 to the food product.

6. A method of producing high-molecular-mass heteropolysaccharides of at least $5 \times 10^6$ Daltons in food fermentation processes comprising adding a functional starter culture or co-culture of the *Streptococcus thermophilus* ST 111 strain according to claim 1 to said food at the start or during the food fermentation process.

7. The method according to claim 5 wherein said food product is a dairy product.

8. The method according to claim 7 wherein said dairy product is selected from the group consisting of milk products, fermented milk drinks, yoghurts, cheeses, sour cream, whipped toppings, quark and kefir.

9. A method of producing high-molecular-mass heteropolysaccharides of at least $5 \times 10^6$ Daltons during fermentation comprising fermenting the co-culture according to claim 3.

10. A method for the fermentation of a food product comprising adding the co-culture according to claim 3 to the food product.

11. The method according to claim 10 wherein said food product is a dairy product.

12. The method according to claim 11 wherein said dairy product is selected from the group consisting of milk products, fermented milk drinks, yoghurts, cheeses, sour cream, whipped toppings, quark and kefir.

13. A method of fermentation of a yoghurt comprising adding the functional starter culture according to claim 2 to the yoghurt.

14. A method of fermentation of mozzarella cheese comprising adding the co-culture according to claim 3 to the mozzarella cheese.

* * * * *

UNITED STATES PATENT AND TRADEMARK OFFICE
CERTIFICATE OF CORRECTION

PATENT NO. : 7,615,367 B2 Page 1 of 1
APPLICATION NO. : 10/516580
DATED : November 10, 2009
INVENTOR(S) : De Vuyst et al.

It is certified that error appears in the above-identified patent and that said Letters Patent is hereby corrected as shown below:

Title Page, (30) Foreign Application Priority Data, "02447104" should be changed to --02447104.7--

Title Page, Column 2, "Other Publications", Line 30, "Budd, et al." should be changed to
 --Bubb, et al.--

Column 3, Lines 35-36, "of at igh-molecular-mass exopolysaccharide of at least" should be changed
 to --of at least--

Column 5, Line 42, "of several startercultures" should be changed to --of several starter cultures--

Column 6, Line 59, "of at least 3gl$^{-1}$ was" should be changed to --of at least 3g.1$^{-1}$ was--

Column 7, Lines 64-65, "the Theological properties" should be changed to --the rheological
 properties--

Column 9, Line 23, "fraction after aceton" should be changed to --fraction after acetone--

Column 9, Line 28, "after aceton precipitation." should be changed to --after acetone precipitation.--

Column 11, Line 12, "quality of bread" should be changed to --quality of bread.--

Column 12, Line 58, "nm (●), colony" should be changed to --nm (■), colony--

Column 12, Line 61, "sucrose (●)," should be changed to --sucrose (■),--

Column 12, Line 67, "Guar gum (●)," should be changed to --Guar gum (■),--

Column 23, Table 7, Line 1, "Lactid acid bacteria*" should be changed to --Lactic acid bacteria*--

Column 23, Table 7, Line 15, "*kefiranofacies*," should be changed to --*kefiranofaciens*,--

Signed and Sealed this

Thirtieth Day of March, 2010

David J. Kappos
*Director of the United States Patent and Trademark Office*